(12) United States Patent
Someya et al.

(10) Patent No.: US 11,617,643 B2
(45) Date of Patent: *Apr. 4, 2023

(54) INTRAOCULAR LENS INSERTION DEVICE

(71) Applicant: HOYA CORPORATION, Tokyo (JP)

(72) Inventors: Kenji Someya, Kasukabe (JP); Takashi Ichinohe, Singapore (SG); Kazunori Kudo, Saku (JP)

(73) Assignee: Hoya Corporation, Tokyo (JP)

( * ) Notice: Subject to any disclaimer, the term of this patent is extended or adjusted under 35 U.S.C. 154(b) by 627 days.

This patent is subject to a terminal disclaimer.

(21) Appl. No.: 16/550,144

(22) Filed: Aug. 23, 2019

(65) Prior Publication Data

US 2020/0113674 A1    Apr. 16, 2020

Related U.S. Application Data

(60) Continuation of application No. 15/063,395, filed on Mar. 7, 2016, now Pat. No. 10,390,940, which is a
(Continued)

(30) Foreign Application Priority Data

May 30, 2007 (JP) ................................. 2007-144262
Sep. 25, 2007 (JP) ................................. 2007-247987

(51) Int. Cl.
*A61F 2/16* (2006.01)

(52) U.S. Cl.
CPC ............ *A61F 2/167* (2013.01); *A61F 2/1678* (2013.01)

(58) Field of Classification Search
CPC ...... A61F 2/1662; A61F 2/167; A61F 2/1672; A61F 2/1678; A61F 2002/16905; A61F 2002/169053
See application file for complete search history.

(56) References Cited

U.S. PATENT DOCUMENTS 2,761,446 A    9/1956 Reed
3,212,685 A    10/1965 Swan
(Continued)

FOREIGN PATENT DOCUMENTS

CN    204601363 U    9/2015
DE    3610925        10/1987
(Continued)

OTHER PUBLICATIONS

U.S. Appl. No. 15/063,395, filed Mar. 7, 2016, US 20160346077A1.
(Continued)

*Primary Examiner* — Sarah W Aleman
(74) *Attorney, Agent, or Firm* — Henricks Slavin LLP

(57) ABSTRACT

An intraocular lens insertion device which dramatically reduces the possibility that a plunger damages an intraocular lens, and which can safely and surely insert an intraocular lens into an eye is provided. An intraocular lens insertion unit comprises a lens disposing part for disposing an intraocular lens, a plunger for pushing out the intraocular lens disposed at the lens disposing part, a transition part for deforming the intraocular lens pushed out by the plunger, and a nozzle for ejecting the deformed intraocular lens. The plunger has a lens contact part for contacting the outer edge of the intraocular lens, and a protrusive part for pushing the lens contact part downward the intraocular lens by the deformation of the intraocular lens, both lens contact part and protrusive part are provided at the leading end of the plunger.

17 Claims, 31 Drawing Sheets

Related U.S. Application Data continuation of application No. 13/244,449, filed on Sep. 24, 2011, now Pat. No. 9,289,288, which is a division of application No. 12/602,442, filed as application No. PCT/JP2008/059996 on May 30, 2008, now Pat. No. 8,747,465.

(56) References Cited

U.S. PATENT DOCUMENTS

| | | |
|---|---|---|
| 4,205,747 A | 6/1980 | Gilliam et al. |
| 4,269,307 A | 5/1981 | LaHaye |
| 4,423,809 A | 1/1984 | Mazzocco |
| 4,573,998 A | 3/1986 | Mazzocco |
| 4,608,049 A | 8/1986 | Kelman |
| 4,634,423 A | 1/1987 | Bailey |
| 4,681,102 A | 7/1987 | Bartell |
| 4,697,697 A | 10/1987 | Graham et al. |
| 4,699,140 A | 10/1987 | Holmes |
| 4,702,244 A | 10/1987 | Mazzocco |
| 4,715,373 A | 12/1987 | Mazzocco et al. |
| 4,747,404 A | 5/1988 | Jampel et al. |
| 4,750,498 A | 6/1988 | Graham |
| 4,759,359 A | 7/1988 | Willis et al. |
| 4,763,650 A | 8/1988 | Hauser |
| 4,765,329 A | 8/1988 | Cumming et al. |
| 4,769,034 A | 9/1988 | Poley |
| 4,781,719 A | 11/1988 | Kelman |
| 4,787,904 A | 11/1988 | Severin |
| 4,810,249 A | 3/1989 | Haber et al. |
| 4,819,631 A | 4/1989 | Poley |
| 4,834,094 A | 5/1989 | Patton |
| 4,836,201 A | 6/1989 | Patton |
| 4,862,885 A | 9/1989 | Cumming |
| 4,880,000 A | 11/1989 | Holmes et al. |
| 4,919,130 A | 4/1990 | Stoy et al. |
| 4,934,363 A | 6/1990 | Smith et al. |
| 4,955,889 A | 9/1990 | Van Gent |
| 4,976,716 A | 12/1990 | Cumming |
| 4,988,352 A | 1/1991 | Poley |
| 4,994,028 A | 2/1991 | Leonard et al. |
| 5,066,297 A | 11/1991 | Cumming |
| 5,098,439 A | 3/1992 | Hill et al. |
| 5,123,905 A | 6/1992 | Kelman |
| 5,139,501 A | 8/1992 | Klaas |
| 5,171,241 A | 12/1992 | Buboltz et al. |
| 5,176,686 A | 1/1993 | Poley |
| 5,178,622 A | 1/1993 | Lehner, II |
| 5,190,552 A | 3/1993 | Kelman |
| 5,190,553 A | 3/1993 | Kanert et al. |
| 5,222,972 A | 6/1993 | Hill et al. |
| 5,242,450 A | 9/1993 | McDonald |
| 5,259,395 A | 11/1993 | Li |
| 5,275,604 A | 1/1994 | Rheinish et al. |
| 5,281,227 A | 1/1994 | Sussman |
| 5,304,182 A | 4/1994 | Rheinish et al. |
| 5,354,333 A | 10/1994 | Kammann et al. |
| 5,395,378 A | 3/1995 | McDonald |
| 5,425,734 A | 6/1995 | Blake |
| 5,454,818 A | 10/1995 | Hambleton et al. |
| 5,468,246 A | 11/1995 | Blake |
| 5,474,562 A | 12/1995 | Orchowski et al. |
| 5,494,484 A | 2/1996 | Feingold |
| 5,496,328 A | 3/1996 | Nakajima et al. |
| 5,499,987 A | 3/1996 | Feingold |
| 5,562,676 A | 10/1996 | Brady et al. |
| 5,571,113 A | 11/1996 | McDonald |
| 5,578,042 A | 11/1996 | Cumming |
| 5,582,613 A | 12/1996 | Brady |
| 5,582,614 A | 12/1996 | Feingold |
| 5,584,304 A | 12/1996 | Brady |
| 5,616,148 A | 4/1997 | Eagles et al. |
| 5,620,450 A | 4/1997 | Eagles et al. |
| 5,643,275 A | 7/1997 | Blake |
| 5,643,276 A | 7/1997 | Zaleski |
| 5,645,534 A | 7/1997 | Chanoch |
| 5,653,715 A | 8/1997 | Reich et al. |
| 5,653,753 A | 8/1997 | Brady et al. |
| 5,702,402 A | 12/1997 | Brady |
| 5,702,441 A | 12/1997 | Zhou |
| 5,716,364 A | 2/1998 | Makker et al. |
| 5,728,075 A | 3/1998 | Levander |
| 5,728,102 A | 3/1998 | Feingold et al. |
| 5,735,858 A | 4/1998 | Makker et al. |
| 5,766,181 A | 6/1998 | Chambers et al. |
| 5,772,666 A * | 6/1998 | Feingold ............... A61F 2/1678 606/107 |
| 5,772,667 A | 6/1998 | Blake |
| 5,776,138 A | 7/1998 | Vidal et al. |
| 5,800,442 A | 9/1998 | Wolf et al. |
| 5,803,925 A | 9/1998 | Yang et al. |
| 5,807,400 A | 9/1998 | Chambers et al. |
| 5,810,833 A | 9/1998 | Brady et al. |
| 5,810,834 A | 9/1998 | Heyman |
| 5,860,984 A | 1/1999 | Chambers et al. |
| 5,860,986 A | 1/1999 | Reich et al. |
| 5,868,751 A | 2/1999 | Feingold |
| 5,868,752 A | 2/1999 | Makker et al. |
| 5,873,879 A | 2/1999 | Figueroa et al. |
| 5,876,406 A | 3/1999 | Wolf et al. |
| 5,876,407 A | 3/1999 | Makker et al. |
| 5,876,440 A | 3/1999 | Feingold |
| 5,891,152 A | 4/1999 | Feingold |
| 5,902,307 A | 5/1999 | Feingold et al. |
| 5,919,197 A | 7/1999 | McDonald |
| 5,921,989 A | 7/1999 | Deacon et al. |
| 5,928,245 A | 7/1999 | Wolf et al. |
| 5,941,886 A | 8/1999 | Feingold |
| 5,942,277 A | 8/1999 | Makker et al. |
| 5,944,725 A | 8/1999 | Cicenas |
| 5,947,974 A | 9/1999 | Brady et al. |
| 5,947,975 A | 9/1999 | Kikuchi et al. |
| 5,957,748 A | 9/1999 | Ichiha |
| 5,957,896 A | 9/1999 | Bendek et al. |
| 6,001,107 A | 12/1999 | Feingold |
| 6,010,510 A | 1/2000 | Brown et al. |
| 6,022,358 A | 2/2000 | Wolf et al. |
| 6,048,348 A | 4/2000 | Chambers et al. |
| 6,050,999 A | 4/2000 | Paraschac et al. |
| 6,051,000 A | 4/2000 | Heyman |
| 6,056,757 A | 5/2000 | Feingold et al. |
| 6,056,758 A | 5/2000 | Vidal et al. |
| 6,059,791 A | 5/2000 | Chambers |
| 6,074,397 A | 6/2000 | Chambers et al. |
| 6,083,230 A | 7/2000 | Makker et al. |
| 6,093,193 A | 7/2000 | Makker et al. |
| 6,129,733 A | 10/2000 | Brady et al. |
| 6,142,999 A | 11/2000 | Brady et al. |
| 6,143,000 A | 11/2000 | Feingold |
| 6,162,229 A | 12/2000 | Feingold et al. |
| 6,174,315 B1 | 1/2001 | Chambers et al. |
| 6,214,015 B1 | 4/2001 | Reich et al. |
| 6,241,737 B1 | 6/2001 | Feingold |
| 6,248,111 B1 | 6/2001 | Glick et al. |
| 6,251,114 B1 | 6/2001 | Farmer et al. |
| 6,254,607 B1 | 7/2001 | Makker et al. |
| 6,267,768 B1 | 7/2001 | Deacon |
| 6,283,975 B1 | 9/2001 | Glick et al. |
| 6,283,976 B1 | 9/2001 | Portney |
| 6,312,433 B1 | 11/2001 | Butts |
| 6,334,862 B1 | 1/2002 | Vidal et al. |
| 6,336,932 B1 | 1/2002 | Figueroa et al. |
| 6,355,046 B2 | 3/2002 | Kikuchi et al. |
| 6,371,960 B2 | 4/2002 | Heyman et al. |
| 6,386,357 B1 | 5/2002 | Egawa |
| 6,387,101 B1 | 5/2002 | Butts et al. |
| 6,398,788 B1 | 6/2002 | Makker et al. |
| 6,406,481 B2 | 6/2002 | Feingold et al. |
| 6,428,545 B2 | 8/2002 | Portney |
| 6,447,519 B1 | 9/2002 | Brady et al. |
| 6,447,520 B1 * | 9/2002 | Ott ........................ A61F 2/1678 606/107 |
| 6,468,282 B2 | 10/2002 | Kikuchi et al. |
| 6,471,708 B2 | 10/2002 | Green |
| 6,491,697 B1 | 12/2002 | Clark et al. |

(56) References Cited

U.S. PATENT DOCUMENTS

| | | | |
|---|---|---|---|
| 6,497,708 B1 * | 12/2002 | Cumming | A61F 2/1664 606/107 |
| 6,500,181 B1 | 12/2002 | Portney | |
| 6,503,275 B1 | 1/2003 | Cumming | |
| 6,506,195 B2 | 1/2003 | Chambers et al. | |
| 6,537,283 B2 | 3/2003 | Van Noy | |
| 6,540,754 B2 | 4/2003 | Brady | |
| 6,554,839 B2 | 4/2003 | Brady | |
| 6,558,395 B2 | 5/2003 | Hjertman et al. | |
| 6,605,093 B1 | 8/2003 | Blake | |
| 6,607,537 B1 | 8/2003 | Binder | |
| 6,629,979 B1 | 10/2003 | Feingold | |
| 6,666,871 B2 | 12/2003 | Kikuchi et al. | |
| 6,679,891 B2 | 1/2004 | Makker et al. | |
| 6,685,740 B2 | 2/2004 | Figueroa et al. | |
| 6,712,848 B1 | 3/2004 | Wolf et al. | |
| 6,723,104 B2 | 4/2004 | Ott | |
| 6,733,507 B2 | 5/2004 | McNicholas et al. | |
| 6,749,631 B1 | 6/2004 | Pietrini et al. | |
| 6,793,674 B2 | 9/2004 | Zapata | |
| 6,858,033 B2 | 2/2005 | Kobayashi | |
| 6,921,405 B2 | 7/2005 | Feingold et al. | |
| 6,923,815 B2 | 8/2005 | Brady et al. | |
| 6,976,989 B1 | 12/2005 | Vincent | |
| 7,014,641 B2 | 3/2006 | Kobayashi et al. | |
| 7,025,782 B2 | 4/2006 | Kobayashi et al. | |
| 7,033,366 B2 | 4/2006 | Brady | |
| 7,037,312 B2 | 5/2006 | Kikuchi et al. | |
| 7,074,227 B2 | 7/2006 | Portney | |
| 7,097,649 B2 | 8/2006 | Meyer | |
| 7,131,976 B2 | 11/2006 | Kobayashi et al. | |
| 7,156,854 B2 | 1/2007 | Brown et al. | |
| 7,348,038 B2 | 3/2008 | Makker et al. | |
| 7,422,604 B2 | 9/2008 | Vaquero et al. | |
| 7,429,263 B2 | 9/2008 | Vaquero et al. | |
| 7,458,976 B2 | 12/2008 | Peterson et al. | |
| 7,476,230 B2 | 1/2009 | Ohno et al. | |
| 7,494,505 B2 | 2/2009 | Kappelhof et al. | |
| 7,645,300 B2 | 1/2010 | Tsai | |
| 8,273,122 B2 | 9/2012 | Anderson | |
| 8,382,769 B2 | 2/2013 | Inoue | |
| 8,460,311 B2 | 6/2013 | Ishii | |
| 8,470,032 B2 | 6/2013 | Inoue et al. | |
| 8,475,526 B2 | 7/2013 | Pynson | |
| 8,475,528 B2 | 7/2013 | Ichinohe et al. | |
| 8,523,877 B2 | 9/2013 | Ichinohe et al. | |
| 8,523,941 B2 | 9/2013 | Ichinohe et al. | |
| 8,535,375 B2 | 9/2013 | Ichinohe et al. | |
| 8,545,512 B2 | 10/2013 | Ichinohe et al. | |
| 8,574,239 B2 | 11/2013 | Ichinohe et al. | |
| 8,603,103 B2 | 12/2013 | Kudo et al. | |
| 8,647,382 B2 | 2/2014 | Kudo et al. | |
| 8,702,795 B2 | 4/2014 | Shoji et al. | |
| 8,747,465 B2 | 6/2014 | Someya et al. | |
| 8,968,328 B2 | 3/2015 | Ichinohe et al. | |
| 9,114,006 B2 | 8/2015 | Inoue | |
| 9,114,007 B2 | 8/2015 | Ichinohe et al. | |
| 9,186,246 B2 | 11/2015 | Inoue | |
| 9,220,593 B2 | 12/2015 | Ichinohe | |
| 9,289,288 B2 | 3/2016 | Someya et al. | |
| 9,314,373 B2 | 4/2016 | Kudo et al. | |
| 9,326,847 B2 | 5/2016 | Sanger | |
| 9,364,320 B2 | 6/2016 | Ichinohe et al. | |
| 9,554,894 B2 | 1/2017 | Inoue | |
| 9,572,710 B1 | 2/2017 | Kudo et al. | |
| 9,655,718 B2 | 5/2017 | Kudo | |
| 9,687,340 B2 | 6/2017 | Anderson | |
| 9,877,826 B2 | 1/2018 | Kudo et al. | |
| 9,901,442 B2 | 2/2018 | Kudo et al. | |
| 9,907,647 B2 | 3/2018 | Inoue | |
| 9,980,811 B2 | 5/2018 | Kudo et al. | |
| 10,039,668 B2 | 8/2018 | Kudo et al. | |
| 10,383,723 B2 | 8/2019 | Kudo | |
| 10,390,940 B2 | 8/2019 | Someya et al. | |
| 10,405,971 B2 | 9/2019 | Someya et al. | |
| 10,517,717 B2 | 12/2019 | Inoue | |
| 10,799,339 B2 | 10/2020 | Kudo et al. | |
| 10,849,738 B2 | 12/2020 | Kudo et al. | |
| 11,033,382 B2 | 6/2021 | Watanabe et al. | |
| 2001/0007942 A1 | 7/2001 | Kikuchi et al. | |
| 2001/0020171 A1 * | 9/2001 | Heyman | A61F 2/1678 606/107 |
| 2002/0103490 A1 | 8/2002 | Brady | |
| 2002/0151904 A1 | 10/2002 | Feingold et al. | |
| 2002/0165610 A1 | 11/2002 | Waldock | |
| 2002/0193805 A1 | 12/2002 | Ott et al. | |
| 2003/0036765 A1 | 2/2003 | Van Noy | |
| 2003/0040755 A1 | 2/2003 | Meyer | |
| 2003/0050647 A1 | 3/2003 | Brady | |
| 2003/0088253 A1 | 5/2003 | Seil | |
| 2003/0139749 A1 | 7/2003 | Kikuchi et al. | |
| 2003/0181921 A1 | 9/2003 | Jeannin | |
| 2003/0195522 A1 * | 10/2003 | McNicholas | A61F 2/1678 606/107 |
| 2003/0212406 A1 | 11/2003 | Kobayashi et al. | |
| 2003/0212407 A1 | 11/2003 | Kikuchi | |
| 2003/0212408 A1 | 11/2003 | Kobayashi | |
| 2003/0212409 A1 | 11/2003 | Kobayashi et al. | |
| 2004/0039345 A1 | 2/2004 | Benz et al. | |
| 2004/0111094 A1 | 6/2004 | Meyer | |
| 2004/0117012 A1 | 6/2004 | Vincent | |
| 2004/0127911 A1 | 7/2004 | Figueroa | |
| 2004/0147938 A1 | 7/2004 | Dusek et al. | |
| 2004/0186428 A1 | 9/2004 | Ray | |
| 2004/0238392 A1 | 12/2004 | Peterson et al. | |
| 2004/0243141 A1 | 12/2004 | Brown et al. | |
| 2005/0033308 A1 | 2/2005 | Callahan et al. | |
| 2005/0049605 A1 | 3/2005 | Vaquero et al. | |
| 2005/0049606 A1 | 3/2005 | Vaquero et al. | |
| 2005/0055011 A1 | 3/2005 | Enggaard | |
| 2005/0125000 A1 | 6/2005 | Tourrette et al. | |
| 2005/0143750 A1 * | 6/2005 | Vaquero | A61F 2/1664 606/107 |
| 2005/0182419 A1 | 8/2005 | Tsai | |
| 2005/0222578 A1 | 10/2005 | Vaquero | |
| 2005/0261703 A1 | 11/2005 | Feingold et al. | |
| 2006/0085013 A1 | 4/2006 | Dusek | |
| 2006/0142781 A1 | 6/2006 | Pynson et al. | |
| 2006/0167466 A1 | 7/2006 | Dusek | |
| 2006/0173540 A1 | 8/2006 | Vincent | |
| 2006/0200167 A1 | 9/2006 | Peterson et al. | |
| 2006/0229633 A1 | 10/2006 | Shepherd | |
| 2006/0235429 A1 | 10/2006 | Lee et al. | |
| 2006/0293694 A1 | 12/2006 | Futamura | |
| 2007/0000801 A1 | 1/2007 | Mauran et al. | |
| 2007/0005135 A1 | 1/2007 | Makker et al. | |
| 2007/0168026 A1 | 7/2007 | Nagasaka | |
| 2007/0173860 A1 | 7/2007 | Iwasaki | |
| 2007/0270945 A1 | 11/2007 | Kobayashi | |
| 2008/0027460 A1 | 1/2008 | Kobayashi | |
| 2008/0033449 A1 | 2/2008 | Cole et al. | |
| 2008/0058830 A1 | 3/2008 | Cole et al. | |
| 2008/0086146 A1 | 4/2008 | Ishii et al. | |
| 2008/0097459 A1 | 4/2008 | Kammerlander et al. | |
| 2008/0221584 A1 | 9/2008 | Downer | |
| 2009/0036898 A1 | 2/2009 | Ichinohe | |
| 2009/0043313 A1 | 2/2009 | Ichinohe | |
| 2009/0112223 A1 | 4/2009 | Downer et al. | |
| 2009/0125034 A1 | 5/2009 | Pynson | |
| 2009/0138022 A1 | 5/2009 | Tu et al. | |
| 2009/0204122 A1 | 8/2009 | Ichinohe et al. | |
| 2009/0216244 A1 | 8/2009 | Pynson | |
| 2009/0248031 A1 | 10/2009 | Ichinohe | |
| 2009/0270876 A1 | 10/2009 | Hoffmann et al. | |
| 2009/0292293 A1 | 11/2009 | Bogaert et al. | |
| 2010/0082037 A1 | 4/2010 | Kobayashi et al. | |
| 2010/0094309 A1 | 4/2010 | Hboukhny et al. | |
| 2010/0106160 A1 | 4/2010 | Tsai | |
| 2010/0161049 A1 | 6/2010 | Inoue | |
| 2010/0185206 A1 | 7/2010 | Ichinohe et al. | |
| 2010/0217273 A1 | 8/2010 | Someya et al. | |
| 2010/0286704 A1 | 11/2010 | Ichinohe et al. | |
| 2010/0331808 A1 | 12/2010 | Py et al. | |
| 2011/0046633 A1 | 2/2011 | Pankin et al. | |

(56) References Cited

U.S. PATENT DOCUMENTS

| | | |
|---|---|---|
| 2011/0046635 A1 | 2/2011 | Pankin et al. |
| 2011/0082463 A1 | 4/2011 | Inoue |
| 2011/0098717 A1 | 4/2011 | Inoue |
| 2011/0144654 A1 | 6/2011 | Isaacs et al. |
| 2011/0172676 A1 | 7/2011 | Chen |
| 2011/0264101 A1 | 10/2011 | Inoue et al. |
| 2011/0270264 A1 | 11/2011 | Shoji et al. |
| 2011/0288557 A1 | 11/2011 | Kudo et al. |
| 2012/0022548 A1 | 1/2012 | Zacharias |
| 2012/0022549 A1 | 1/2012 | Someya et al. |
| 2012/0071887 A1 | 3/2012 | Ichinohe et al. |
| 2012/0123438 A1 | 5/2012 | Horvath et al. |
| 2012/0221102 A1 | 8/2012 | Tanaka et al. |
| 2013/0006259 A1 | 1/2013 | Sanger |
| 2013/0018460 A1 | 1/2013 | Anderson |
| 2013/0085507 A1 | 4/2013 | Nagasaka |
| 2013/0226193 A1 | 8/2013 | Kudo et al. |
| 2013/0245635 A1 | 9/2013 | Inoue |
| 2013/0345713 A1 | 12/2013 | Cole et al. |
| 2014/0081284 A1 | 3/2014 | Ichinohe et al. |
| 2014/0107660 A1 | 4/2014 | Ichinohe et al. |
| 2014/0114323 A1 | 4/2014 | Kudo et al. |
| 2014/0135784 A1 | 5/2014 | Maroscheck |
| 2014/0180299 A1 | 6/2014 | Ichinohe et al. |
| 2014/0180300 A1 | 6/2014 | Ichinohe et al. |
| 2014/0194890 A1 | 7/2014 | Kudo et al. |
| 2014/0200588 A1 | 7/2014 | Anderson et al. |
| 2014/0276901 A1 | 9/2014 | Auld |
| 2014/0296863 A1 | 10/2014 | Anderson et al. |
| 2015/0157500 A1 | 6/2015 | Midorikawa |
| 2015/0327992 A1 | 11/2015 | Wagner et al. |
| 2016/0000556 A1 | 1/2016 | Perera |
| 2016/0058554 A1 | 3/2016 | Anderson et al. |
| 2016/0113759 A1 | 4/2016 | Inoue |
| 2016/0151150 A1 | 6/2016 | Sato |
| 2016/0193038 A1 | 7/2016 | Kudo et al. |
| 2016/0256316 A1 | 9/2016 | Van Noy et al. |
| 2016/0270907 A1 | 9/2016 | Attinger |
| 2016/0331587 A1 | 11/2016 | Yamada et al. |
| 2016/0346077 A1 | 12/2016 | Someya et al. |
| 2017/0079772 A1 | 3/2017 | Kudo |
| 2017/0119522 A1 | 5/2017 | Auld et al. |
| 2017/0151056 A1 | 6/2017 | Inoue |
| 2017/0202662 A1 | 7/2017 | Someya et al. |
| 2017/0252149 A1 | 9/2017 | Kudo et al. |
| 2017/0252150 A1 | 9/2017 | Kudo et al. |
| 2017/0258582 A1 | 9/2017 | Kudo et al. |
| 2017/0354493 A1 | 12/2017 | Andersen et al. |
| 2018/0014996 A1 | 1/2018 | Asbaghi |
| 2018/0200046 A1 | 7/2018 | Brown et al. |
| 2018/0250125 A1 | 9/2018 | Kudo et al. |
| 2018/0353287 A1 | 12/2018 | Kudo et al. |
| 2019/0151078 A1 | 5/2019 | Watanabe et al. |
| 2019/0192284 A1 | 6/2019 | Watanabe et al. |
| 2021/0145570 A1 | 5/2021 | Kudo |
| 2021/0161653 A1 | 6/2021 | Noda et al. |
| 2022/0151767 A1 | 5/2022 | Kudo |

FOREIGN PATENT DOCUMENTS

| | | |
|---|---|---|
| DE | 4110278 | 10/1992 |
| DE | 19544119 A1 | 5/1997 |
| DE | 20219445 U1 | 3/2003 |
| EP | 0363213 | 4/1990 |
| EP | 0727966 | 9/2003 |
| EP | 1360947 A1 | 11/2003 |
| EP | 1502559 A1 | 7/2004 |
| EP | 1502559 A1 | 2/2005 |
| EP | 1790317 A2 | 5/2007 |
| EP | 1808150 A1 | 7/2007 |
| EP | 1832247 A1 | 9/2007 |
| EP | 1338254 | 12/2008 |
| EP | 2074961 A1 | 7/2009 |
| EP | 2255751 A1 | 12/2010 |
| EP | 2286763 A1 | 2/2011 |
| EP | 2286764 A1 | 2/2011 |
| EP | 2368526 A1 | 9/2011 |
| EP | 2574308 A2 | 4/2013 |
| EP | 2853236 A2 | 4/2015 |
| FR | 2749752 A | 12/1997 |
| JP | 63-197453 A | 8/1988 |
| JP | 4-212350 A | 8/1992 |
| JP | 5-103803 A | 4/1993 |
| JP | 5-103808 | 4/1993 |
| JP | 5-103809 | 4/1993 |
| JP | 08-019558 A | 1/1996 |
| JP | 8-024282 A | 1/1996 |
| JP | 8-505540 | 6/1996 |
| JP | 9-506285 A | 6/1997 |
| JP | 11-113939 A | 4/1999 |
| JP | 11-506357 A | 6/1999 |
| JP | 2000-516487 A | 12/2000 |
| JP | 2000-516488 A | 12/2000 |
| JP | 2001-502563 | 2/2001 |
| JP | 2001-104347 A | 4/2001 |
| JP | 2001-259033 | 9/2001 |
| JP | 2002-516709 A | 6/2002 |
| JP | 2002-355268 A | 12/2002 |
| JP | 2002-541912 A | 12/2002 |
| JP | 2003-144480 A | 5/2003 |
| JP | 3412106 B2 | 6/2003 |
| JP | 2003-210498 A | 7/2003 |
| JP | 2003-527162 A | 9/2003 |
| JP | 2003-325569 A | 11/2003 |
| JP | 2003-325570 A | 11/2003 |
| JP | 2003-325572 A | 11/2003 |
| JP | 2004-024854 A | 1/2004 |
| JP | 2004-041271 A | 2/2004 |
| JP | 2004-188194 A | 7/2004 |
| JP | 2004-344213 A | 12/2004 |
| JP | 2004-351196 A | 12/2004 |
| JP | 2006-014963 A | 1/2006 |
| JP | 2006-181269 A | 7/2006 |
| JP | 2006-297146 A | 11/2006 |
| JP | 2006-333924 A | 12/2006 |
| JP | 2006-333981 A | 12/2006 |
| JP | 2007-503872 A | 3/2007 |
| JP | 2007-152010 A | 6/2007 |
| JP | 2007-181604 A | 7/2007 |
| JP | 2007-222309 A | 9/2007 |
| JP | 2007-244570 A | 9/2007 |
| JP | 2007-526091 A | 9/2007 |
| JP | 2007-307168 A1 | 11/2007 |
| JP | 2008-012016 A | 1/2008 |
| JP | 2008-521535 A | 6/2008 |
| JP | 2008-212689 A | 9/2008 |
| JP | 2008-237274 A | 10/2008 |
| JP | 2009-028233 A | 2/2009 |
| JP | 2009-072221 A | 4/2009 |
| JP | 2011-019987 A | 2/2011 |
| JP | 2011-087976 A | 5/2011 |
| JP | 2011-160858 A | 8/2011 |
| JP | 2011-160859 A | 8/2011 |
| JP | 2013-144163 A | 7/2013 |
| JP | 2014-050484 A | 3/2014 |
| JP | 2014-079630 A | 5/2014 |
| JP | 2016-137122 A | 8/2016 |
| WO | WO9407436 A1 | 4/1994 |
| WO | WO9513022 A1 | 5/1995 |
| WO | WO9628122 A1 | 9/1996 |
| WO | WO9715253 A1 | 5/1997 |
| WO | WO9812969 A1 | 4/1998 |
| WO | WO9937247 A1 | 7/1999 |
| WO | WO9958086 A1 | 11/1999 |
| WO | WO9959668 A1 | 11/1999 |
| WO | WO0045746 A1 | 8/2000 |
| WO | WO0062712 A1 | 10/2000 |
| WO | WO2002071982 A1 | 9/2002 |
| WO | WO2002096322 A1 | 12/2002 |
| WO | WO2004/041323 A2 | 5/2004 |
| WO | WO2004105649 A1 | 12/2004 |
| WO | WO2005023154 A1 | 3/2005 |
| WO | WO2005070341 A1 | 8/2005 |
| WO | WO2005084588 A1 | 9/2005 |

(56) References Cited

FOREIGN PATENT DOCUMENTS

| | | | |
|---|---|---|---|
| WO | WO2006070628 A1 | 7/2006 | |
| WO | WO2006080191 A1 | 8/2006 | |
| WO | WO2006090531 A1 | 8/2006 | |
| WO | WO-2007037223 A1 * | 4/2007 | ............ A61F 2/167 |
| WO | WO2007037223 A1 | 4/2007 | |
| WO | WO2007097221 A1 | 4/2007 | |
| WO | WO2007080869 A1 | 7/2007 | |
| WO | WO2008149794 A1 | 12/2008 | |
| WO | WO2008149795 A1 | 12/2008 | |
| WO | WO2009058929 A1 | 7/2009 | |
| WO | WO2009148091 A1 | 12/2009 | |
| WO | WO2010028873 A1 | 3/2010 | |
| WO | WO2010064670 A1 | 6/2010 | |
| WO | WO2011126144 A1 | 10/2011 | |
| WO | WO2011155636 A1 | 12/2011 | |
| WO | WO2012086797 A1 | 6/2012 | |
| WO | WO2012155887 A1 | 11/2012 | |
| WO | WO2015012312 A1 | 1/2015 | |
| WO | WO2016191764 A1 | 12/2016 | |

OTHER PUBLICATIONS

U.S. Appl. No. 15/476,717, filed Mar. 31, 2017, US 20170202662A1.
U.S. Appl. No. 15/382,377, filed Dec. 16, 2016, US 20170151056A1.
U.S. Appl. No. 15/126,277, filed Sep. 14, 2016, US 20170079772A1.
U.S. Appl. No. 15/756,565, filed Feb. 28, 2018, US 20180250125A1.
U.S. Appl. No. 15/756,569, filed Feb. 28, 2018, US 20180353287A1.
U.S. Appl. No. 16/313,184, filed Dec. 26, 2018, US 20190151078A1.
U.S. Appl. No. 15/600,679, filed May 19, 2017, US Pat. 9,877,826.
U.S. Appl. No. 17/435,762, filed Sep. 2, 2021.
U.S. Appl. No. 13/244,454, filed Sep. 24, 2011, U.S. Pat. No. 8,535,375.
U.S. Appl. No. 11/84,508, filed Jul. 23, 2007, U.S. Pat. No. 8,545,512.
U.S. Appl. No. 12/602,442, filed Dec. 15, 2009, U.S. Pat. No. 8,747,465.
U.S. Appl. No. 13/244,449, filed Sep. 24, 2011, U.S. Pat. No. 9,289,288.
U.S. Appl. No. 15/063,395, filed Mar. 7, 2016, U.S. Pat. No. 10,390,940.
U.S. Appl. No. 15/476,717, filed Mar. 31, 2017, U.S. Pat. No. 10,405,971.
U.S. Appl. No. 12/602,454, filed Dec. 15, 2009, U.S. Pat. No. 8,475,528.
U.S. Appl. No. 13/244,452, filed Sep. 24, 2011, U.S. Pat. No. 8,535,375.
U.S. Appl. No. 12/667,510, filed Dec. 31, 2009, U.S. Pat. No. 9,114,006.
U.S. Appl. No. 14/812,104, filed Jul. 29, 2015, U.S. Pat. No. 9,907,647.
U.S. Appl. No. 12/995,263, filed Dec. 15, 2010, U.S. Pat. No. 9,554,894.
U.S. Appl. No. 15/382,377, filed Dec. 16, 2016, U.S. Pat. No. 10,517,717.
U.S. Appl. No. 12/997,651, filed Dec. 13, 2010, U.S. Pat. No. 8,382,769.
U.S. Appl. No. 13/757,790, filed Feb. 2, 2012, U.S. Pat. No. 9,186,246.
U.S. Appl. No. 13/583,216, filed Apr. 6, 2011, U.S. Pat. No. 9,326,847.
U.S. Appl. No. 15/336,678, filed Oct. 27, 2016, U.S. Pat. No. 9,572,710.
U.S. Appl. No. 11/816,676, filed May 20, 2007, U.S. Pat. No. 8,523,877.
U.S. Appl. No. 12/088,328, filed May 27, 2008, U.S. Pat. No. 8,574,239.
U.S. Appl. No. 13/699,708, filed Jun. 8, 2011, U.S. Pat. No. 8,647,382.
U.S. Appl. No. 14/145,846, filed Dec. 31, 2013, U.S. Pat. No. 9,314,373.
U.S. Appl. No. 15/071,880, filed Mar. 16, 2016, U.S. Pat. No. 10,039,668.
U.S. Appl. No. 15/336,678, filed Nov. 27, 2016, U.S. Pat. No. 9,572,710.
U.S. Appl. No. 15/608,895, filed May 30, 2017, U.S. Pat. No. 9,980,811.
U.S. Appl. No. 13/059,401, filed Feb. 16, 2011, U.S. Pat. No. 8,702,795.
U.S. Appl. No. 13/061,143, filed Feb. 26, 2011, U.S. Pat. No. 8,470,032.
U.S. Appl. No. 13/143,322, filed Jul. 5, 2011, U.S. Pat. No. 8,603,103.
U.S. Appl. No. 14/099,989, filed Dec. 8, 2013, U.S. Pat. No. 9,655,718.
U.S. Appl. No. 15/600,679, filed May 19, 2017, U.S. Pat. No. 9,877,826.
U.S. Appl. No. 15/600,684, filed May 19, 2017, U.S. Pat. No. 9,901,442.
U.S. Appl. No. 11/814,508, filed Jul. 23, 2007, U.S. Pat. No. 8,545,512.
U.S. Appl. No. 14/033,888, filed Sep. 23, 2013, U.S. Pat. No. 9,220,593.
U.S. Appl. No. 11/816,676, filed Aug. 20, 2007, U.S. Pat. No. 8,523,877.
U.S. Appl. No. 13/966,209, filed Aug. 13, 2013, U.S. Pat. No. 9,364,320.
U.S. Appl. No. 12/095,172, filed May 28, 2008, U.S. Pat. No. 8,523,941.
U.S. Appl. No. 14/011,018, filed Aug. 27, 2013, U.S. Pat. No. 8,968,328.
U.S. Appl. No. 12/088,328, filed Mar. 27, 2008, U.S. Pat. No. 8,574,239.
U.S. Appl. No. 14/065,365, filed Oct. 28, 2013, U.S. Pat. No. 9,114,007.
U.S. Appl. No. 11/722,601, filed Apr. 10, 2008, U.S. Pat. No. 8,460,311.
U.S. Appl. No. 15/126,277, filed Sep. 14, 2016, U.S. Pat. No. 10,383,723.
U.S. Appl. No. 15/756,565, filed Feb. 28, 2018, U.S. Pat. No. 10,849,738.
U.S. Appl. No. 15/756,569, filed Feb. 28, 2018, U.S. Pat. No. 10,799,339.
U.S. Appl. No. 16/313,180, filed Dec. 26, 2018, US 20190192284A1.
U.S. Appl. No. 16/313,184, filed Dec. 26, 2018, U.S. Pat. No. 11,033,382.
U.S. Appl. No. 17/055,253, filed Nov. 13, 2020, US 20210161653A1.
U.S. Appl. No. 17/055,186, filed Nov. 13, 2020, US 20210145570A1.
U.S. Appl. No. 17/435,762, filed Sep. 2, 2021, US 20220151767A1.
U.S. Appl. No. 17/801,364, filed Aug. 22, 2022.
Presentation given by James P. McCulley, titled "Benefits of Newest Generation Fully Preloaded Aspheric IOL Delivery System," on Sep. 16, 2008 at the "AsphericIOLs" free paper session of the 2008 Congress of the European Society of Cataract and Refractive Surgery, in Berlin, Germany.

* cited by examiner

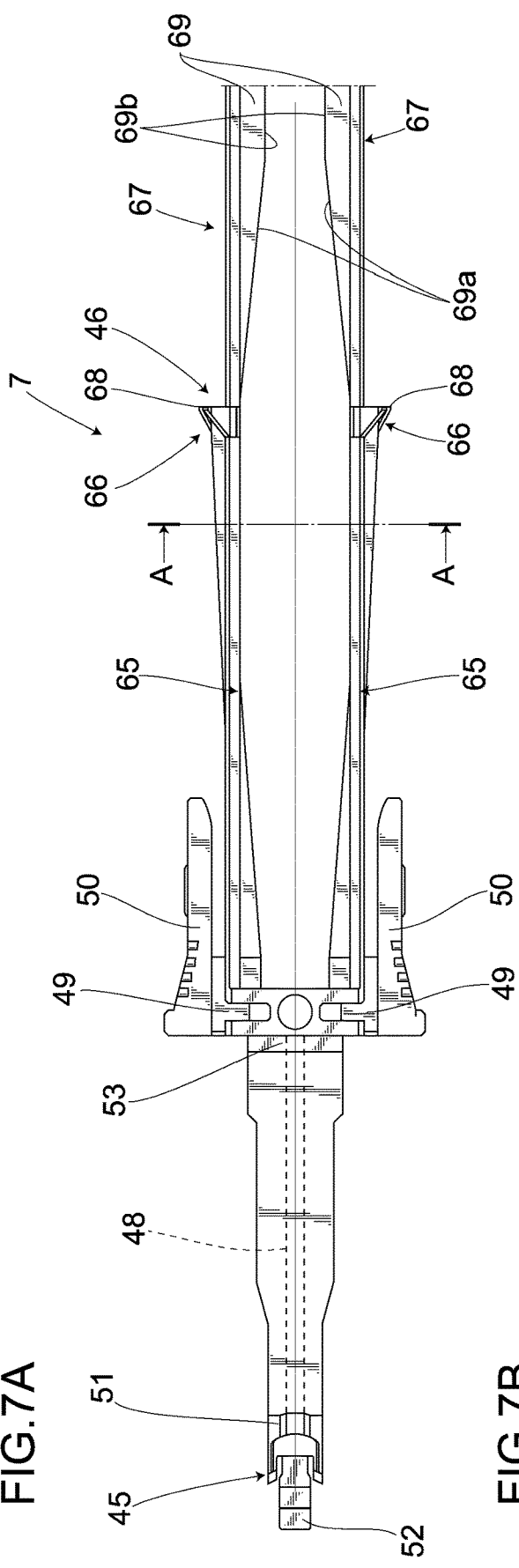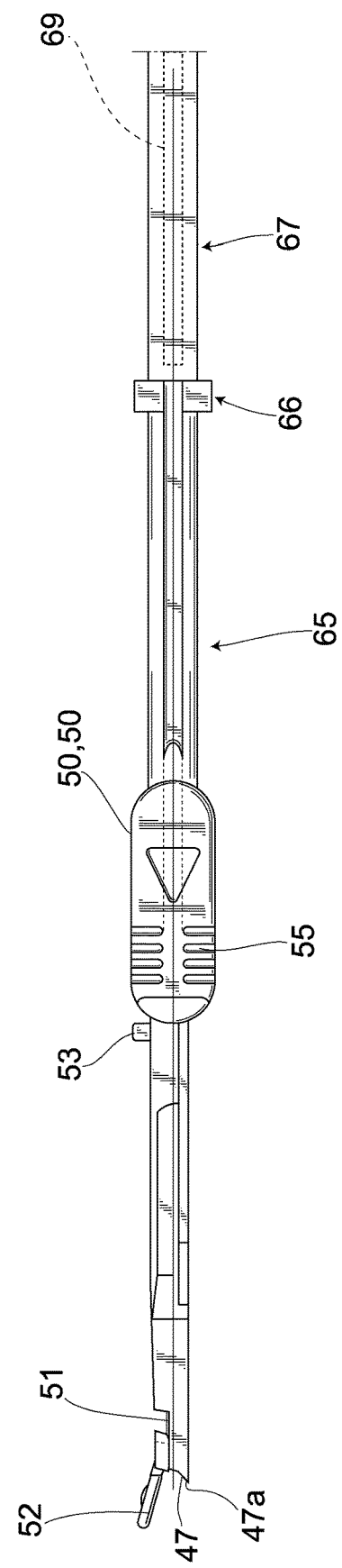

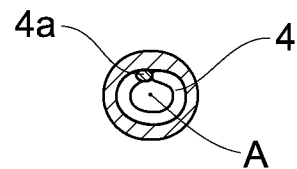
FIG.30E
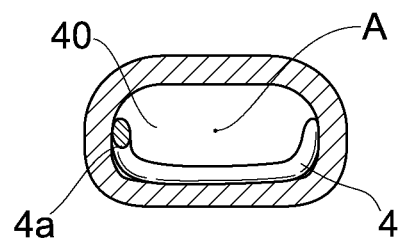
FIG.30D
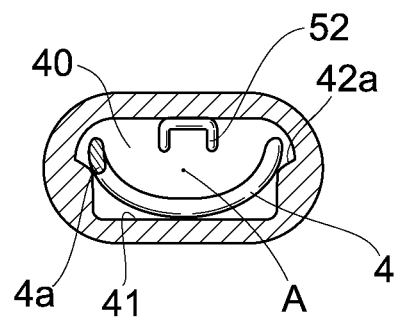
FIG.30C
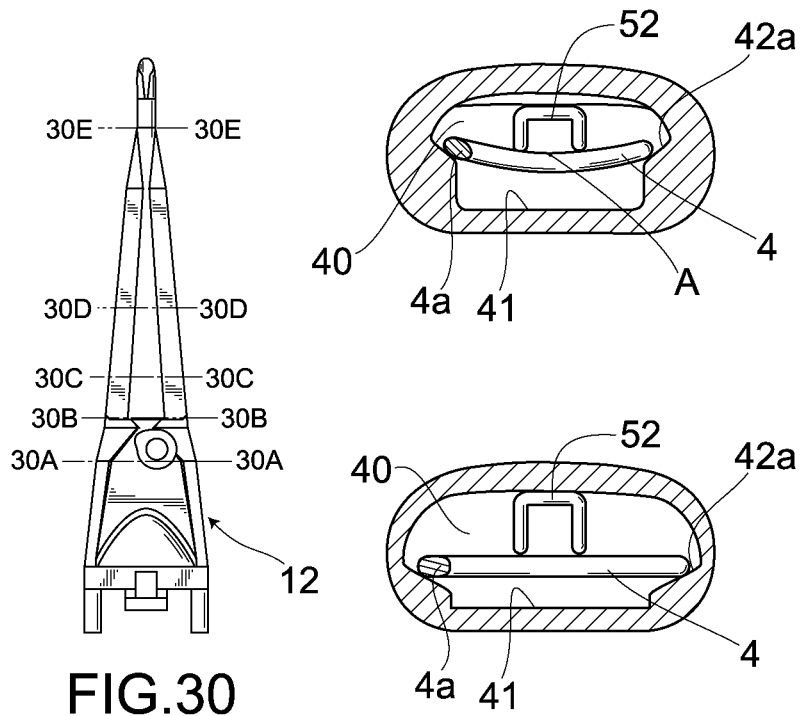
FIG.30B
FIG.30A
FIG.30

INTRAOCULAR LENS INSERTION DEVICE

CROSS-REFERENCE TO RELATED APPLICATIONS

This application is a continuation of U.S. application Ser. No. 15/063,395, filed Mar. 7, 2016, now U.S. Pat. No. 10,390,940, which is a continuation of U.S. application Ser. No. 13/244,449, filed Sep. 24, 2011, now U.S. Pat. No. 9,289,288, which is a divisional of application Ser. No. 12/602,442, having a 371(c) date of Dec. 15, 2009, now U.S. Pat. No. 8,747,465, which is the U.S. National Stage of PCT app. Ser. No. PCT/JP2008/059996, filed May 30, 2008, each of which is incorporated herein by reference in its entirety.

TECHNICAL FIELD

The present invention relates to an intraocular lens insertion device used for inserting an intraocular lens or a phakic intraocular lens into an aphakic eye that has undergone a cataract surgery or phakic eye in a refractive surgery.

BACKGROUND ART

Elimination of an opacified crystal lens through an ultrasonic emulsification and implantation of a lens into an eye that has undergone the elimination of the crystal lens are commonly carried out in cataract surgeries. Nowadays, a soft intraocular lens made of a soft material, such as a silicon elastomer or a soft acrylic material, is used, an optical part of the intraocular lens is folded by an intraocular lens insertion device, and the intraocular lens in this state is pushed by a plunger to push out the lens from a nozzle, and is inserted into an eye through an incision which is smaller than the diameter of the optical part.

Intraocular lens insertion devices can insert an intraocular lens into an eye through a tiny incision, thereby reducing the possibilities of a corneal astigmatism or an infection disease after a surgery. To further reduce the possibility of a corneal astigmatism or an infection disease after a surgery, it is desirable to minimize an incision for inserting an intraocular lens into an eye as much as possible.

To minimize an incision, however, it is necessary to fold an intraocular lens in a smaller size with the miniaturization of the incision. Folding an intraocular lens in a smaller size increases elastic restoring force of the intraocular lens, so that a slide resistance applied to a plunger becomes large in pushing out the intraocular lens from a nozzle by the plunger.

When the slide resistance applied to the plunger becomes large on some level, the leading end of the plunger may run on the face of the optical part of the intraocular lens. Accordingly, even if the intraocular lens is inserted into an eye, the intraocular lens may be damaged by the leading end of the plunger, so that it is difficult in some cases to obtain a desired property of the intraocular lens appropriately.

To overcome such a problem, there is disclosed an intraocular lens insertion device which captures an intraocular lens disposed on a lens disposing part without no load by a plunger having a slot formed at the leading end thereof from a position parallel to the intraocular lens, and prevents the plunger from running on the intraocular lens when releasing the intraocular lens (for example, in Patent Document 1).

Further, there is also disclosed another intraocular lens insertion device having a circular nose part, offset asymmetrically with respect to the central line of a cartridge lumen, and provided at the leading end of a plunger (for example, in Patent Document 1). According to this intraocular lens insertion device, the plunger is urged in such a way that the nose part is pressed against the lower part of the cartridge lumen, and is caused to slide the lower part of the cartridge lumen by such urging force, thereby preventing the nose part from running on an intraocular lens.

Patent Document 1: Japanese Un-Examined Patent Application Publication No. H9-506285
Patent Document 2: Japanese Un-Examined Patent Application Publication No. 2002-516709

DISCLOSURE OF THE INVENTION

Problems to be Solved by the Invention

According to Patent Document 1, however, it is structured to cause the leading end of the plunger itself to clip an intraocular lens, so that a positioning between the intraocular lens and the leading end of the plunger requires a high precision. Further, if the intraocular lens is moved from the lens disposing part because of some reasons, there is a possibility that the intraocular lens is not ejected out because the plunger cannot capture the intraocular lens through portions other than the slot. Even if the intraocular lens is ejected out, the leading end of the plunger highly possibly damages the optical part or a support part of the intraocular lens. Still further, in pressing out the intraocular lens by the plunger, it is thought that the intraocular lens coming in contact with the plunger are significantly deformed, and in releasing the intraocular lens in a crystal lens, there is a possibility that the intraocular lens is not easily released from the slot of the plunger because of the significant deformation of the intraocular lens. It is expected that the groove of the slot is produced in such a manner as to have some versatilities in its height, so that depending on the degree of an intraocular lens, a gap between the height of the groove of the slot and the lens becomes large, and it may be difficult to control the movement of the intraocular lens in ejecting the intraocular lens in the crystal lens.

According to Patent Document 2, however, a large load is always applied to the plunger while the plunger is contacting the internal wall of the cartridge, and because the load applied to the plunger is large, the plunger is fatigued, damaged, and is subjected to a plastic deformation by using the apparatus repeatedly, so that such a plunger may damage an intraocular lens. Therefore, to prevent the fatigue, damage, and plastic deformation of the plunger, the selection of the material of the plunger is limited.

It is an object of the invention to provide an intraocular lens insertion device which dramatically reduces the possibility that a plunger damages an intraocular lens, and which can safely and surely insert an intraocular lens into an eye.

Means for Solving the Problems

To achieve the object, an intraocular lens insertion device according to a first aspect of the invention comprises: a lens disposing part where an intraocular lens is disposed; a plunger which pushes out the intraocular lens disposed on the lens disposing part; a transition part for deforming the intraocular lens pushed out by the plunger; and a nozzle which ejects out the deformed intraocular lens, and wherein the plunger has a lens contact part which contacts an outer edge of the intraocular lens, and a protrusive part which pushes the lens contact part toward a disposing-part bottom face of the lens disposing part where the intraocular lens is disposed, by the deformed intraocular lens, both lens contact part and protrusive part being formed at a leading end of the plunger.

According to a second aspect of the invention, the protrusive part may protrude toward a front of a lens traveling direction upwardly the intraocular lens and beyond the lens contact part.

According to a third aspect of the invention, the protrusive part may have a top face formed in a smoothly curved convex plane.

According to a fourth aspect of the invention, the lens contact part may be formed in a planer shape.

According to a fifth aspect of the invention, the lens contact part may have one end corner, which is on a bottom face side of the lens disposing part, and is formed in a shape like a letter R having a curvature radius less than or equal to 70% of the thickness of the outer edge of the intraocular lens.

According to a sixth aspect of the invention, the plunger may have a rod like axial member, and the lens contact part may be formed in a manner protruding from the axial part toward the bottom face of the lens disposing part.

According to a seventh aspect of the invention, the plunger may be formed of a synthetic resin.

According to an eighth aspect of the invention, the intraocular lens may be disposed on the lens disposing part beforehand.

Effects of the Invention

According to the intraocular lens insertion device set forth in the first aspect of the invention, the protrusive part pushes the lens contact part downwardly the intraocular lens by the deformation of the intraocular lens, a possibility that the intraocular lens is damaged is further reduced, and the intraocular lens can be inserted into an eye surely and safely.

According to the intraocular lens insertion device set forth in the second aspect of the invention, the protrusive part surely pushes the lens contact part downwardly the intraocular lens by the deformation of the intraocular lens.

According to the intraocular lens insertion device set forth in the third aspect of the invention, it is possible to prevent the optical part from being damaged due to the upper face of the protrusive part.

According to the intraocular lens insertion device set forth in the fourth aspect of the invention, it is easy to position the intraocular lens and the leading end of the plunger.

According to the intraocular lens insertion device set forth in the fifth aspect of the invention, the lens contact part contacts the outer edge of the intraocular lens with a large area, and frictional force in a direction vertical to the lens traveling direction is increased, resulting in the prevention of the leading end of the plunger from running on the optical part.

According to the intraocular lens insertion device set forth in the sixth aspect of the invention, even if the one end corner is lifted up from the bottom of a cartridge lumen, the one end corner can bite into the outer edge of the intraocular lens, thereby achieving an anchor effect.

According to the intraocular lens insertion device set forth in the seventh aspect of the invention, the device can be mass-produced at a low cost, and can be used as a disposal type. Furthermore, the leading end and the axial end part can deform, so that an application of an excessive load to the intraocular lens can be prevented, thereby preventing the intraocular lens from being damaged.

According to the intraocular lens insertion device set forth in the eighth aspect of the invention, an operation of loading the intraocular lens into the intraocular lens insertion device becomes unnecessary in a surgery, thereby reducing a possibility of a mishandling. Furthermore, the lens contact part can be selected in accordance with the thickness of the outer edge of the intraocular lens, thus it is possible to further surely prevent the leading end of the plunger from running on the optical part.

BRIEF DESCRIPTION OF THE DRAWINGS

FIG. 7A is a top plan view showing the structure of a slider and FIG. 7B is a side view thereof;

FIG. 30 is a is a plan view of the leading end member and FIGS. 30A-30E are partial cross-section views thereof showing the operation of the device step by step;

BEST MODE FOR CARRYING OUT THE INVENTION

Hereinafter will be explained preferred embodiments of the invention with reference to the accompanying drawings.

1. General Structure

Figure 1:
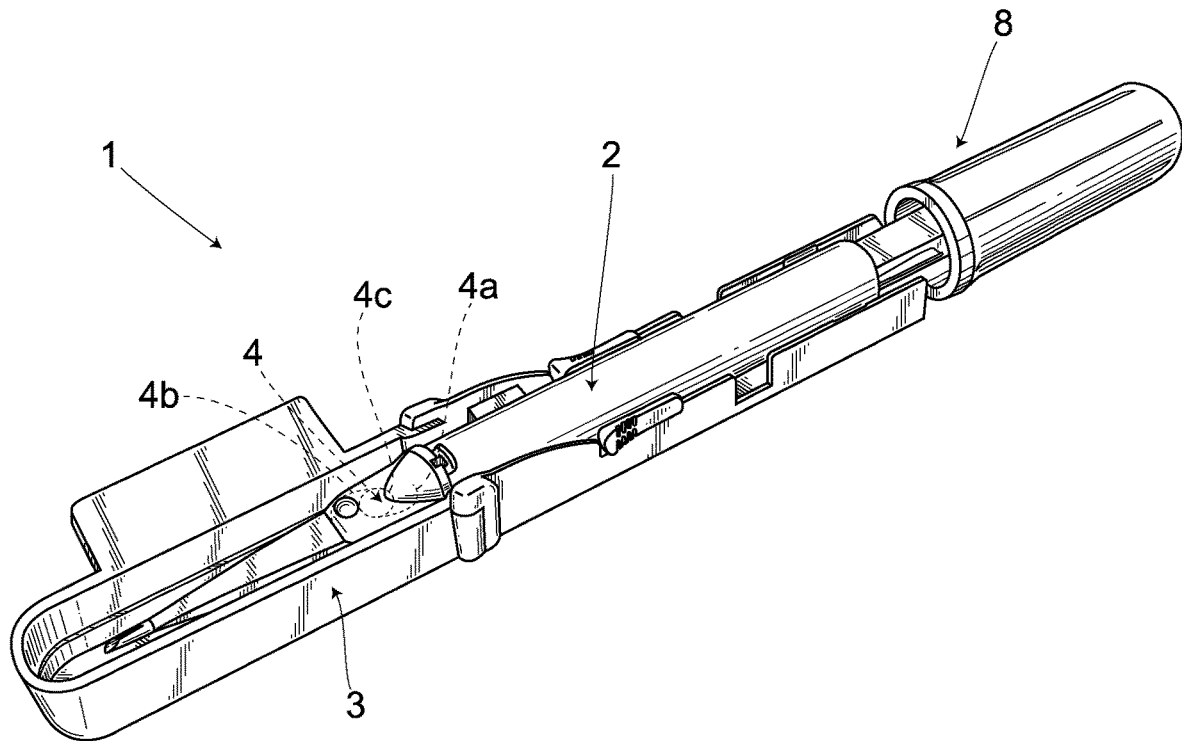
FIG. 1 is a perspective view showing the structure of an intraocular lens insertion device according to an embodiment of the invention.

An intraocular lens insertion device 1 shown in FIG. 1 comprises an intraocular lens insertion unit 2 and a casing 3, and is structured in such a way that the intraocular lens insertion unit 2 in which an intraocular lens 4 is loaded beforehand is placed in the casing 3. The intraocular lens insertion unit 2 is placed in the casing 3 in this manner, thereby preventing the intraocular lens 4 loaded in the intraocular lens insertion unit 2 beforehand from accidentally being ejected out therefrom, and from being damaged during a delivery thereof, and prior to a surgery such as at a presurgery preparation after shipment of the intraocular lens insertion device 1 from a manufacturing factory. Forming the overall intraocular lens insertion device 1 mainly of a synthetic resin facilitates a mass production thereof, thus suitable for a disposal application. Note that in the following explanations, the front of a lens traveling axis as a lens traveling direction is simply called "front", and the rear of the lens traveling axis is simply called "rear".

(1) Intraocular Lens Insertion Unit

Figure 2:
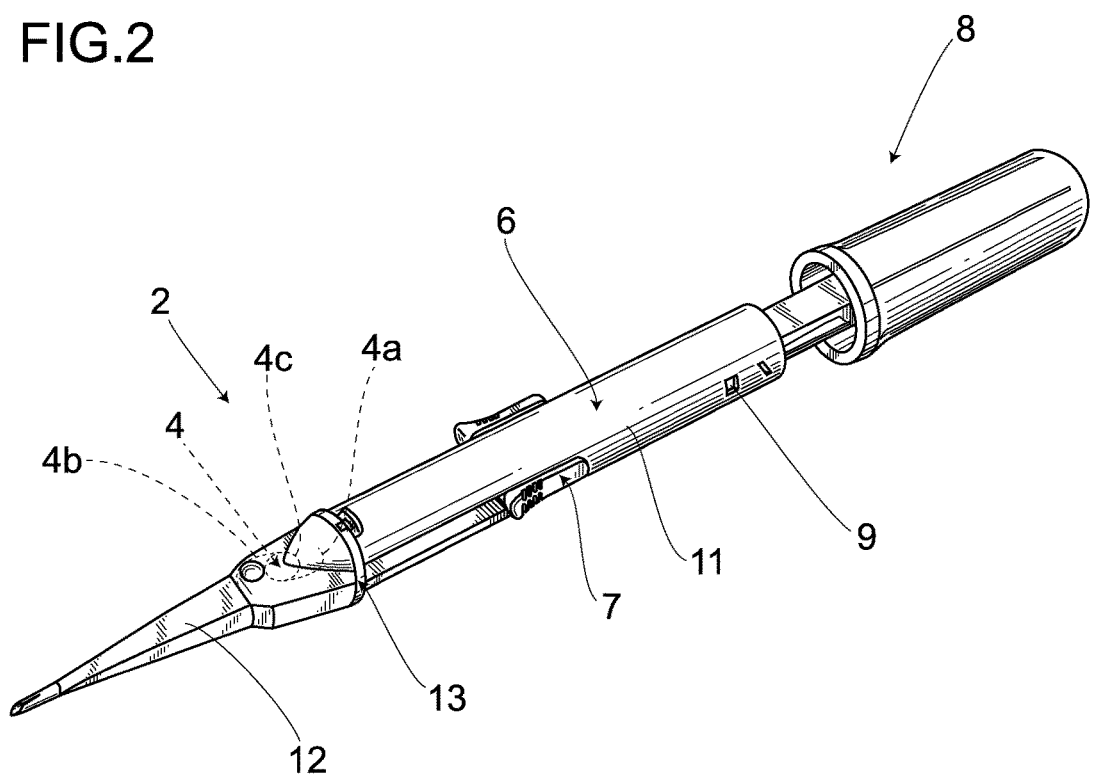
FIG. 2 is a perspective view showing the structure of the intraocular lens insertion device.

As shown in FIG. 2, the intraocular lens insertion unit 2 has a main body 6, a slider 7, a plunger 8, and a lock mechanism 9. The slider 7 and the plunger 8 are provided in a manner capable of moving frontward and rearward in the main body 6. The lock mechanism 9 limits a frontward movement of the plunger 8. The lock mechanism 9 is released as the slider 7 is moved frontward, and then the plunger 8 becomes movable frontward. The intraocular lens insertion unit 2 structured in this manner pushes out the intraocular lens 4 by the slider 7 at first, surely folds the intraocular lens 4 in a predetermined shape, and then pushes out the intraocular lens 4 by the plunger 8, to thereby fold down the intraocular lens compactly, thus allowing the intraocular lens 4 to be inserted into an eye. Accordingly, the intraocular lens insertion unit 2 is designed to allow the lock mechanism 9 to reliably prevent the plunger 8 from pushing out the intraocular lens 4 before the slider 7 pushes out the intraocular lens 4, and to fold down the intraocular lens 4 disposed in the main body 6 through two stages first by the slider 7 and then by the plunger 8 while moving the intraocular lens 4 frontward.

(a) Main Body

The main body 6 comprises a cylindrical basal end member 11 and a tapered leading end member 12. The basal end member 11 and the leading end member 12 are detachably coupled together by a first coupler 13, thus integrated together.

As shown in FIG. 3, the basal end member 11 has a lens disposing part 15, an engagement part 16, slider guides 17, a stopper 18, first latching openings 19, and an engagement protrusion 20.

Figure 4:
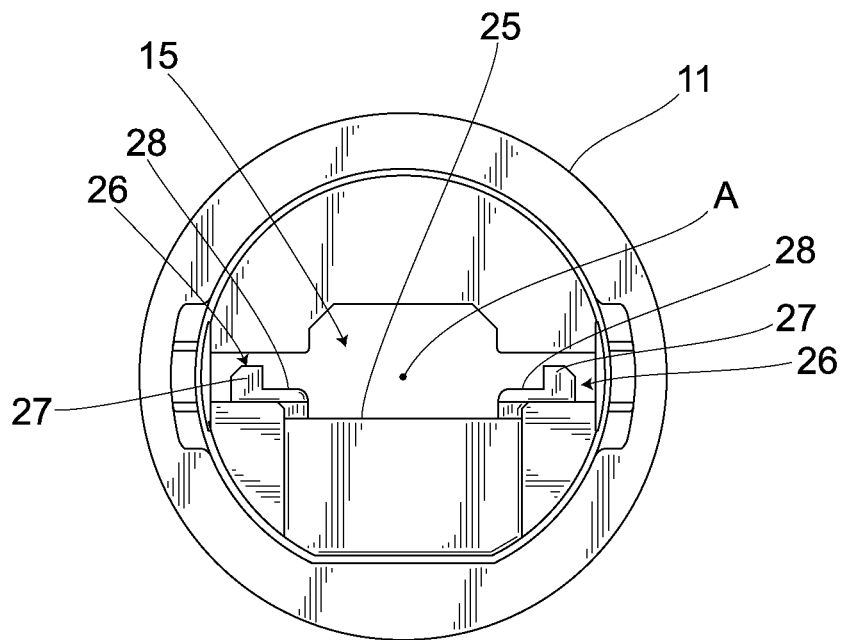
FIG. 4 is a diagram showing the structure of a lens disposing part.

The lens disposing part 15 is formed of a tabular member protruding frontward from a front one end. As shown in FIG. 4, the lens disposing part 15 has a disposing-part bottom face 25 formed horizontal along the lens traveling axis A, and a disposing frame 26 formed at both ends of the disposing-part bottom face 25 parallel to the lens traveling axis A and across the lens traveling axis A. The disposing frame 26 has frame bodies 27, 27 and base end rails 28, 28. Wall-like frame bodies 27, 27 are provided in a standing manner, surrounding the disposing-part bottom face 25 so as to be provided across the lens traveling axis A, and the base end rails 28, 28 are formed integral with the frame bodies 27, 27 in a manner protruding upward the disposing bottom face 25. Note that in this specification, a disposing-part bottom face 25 side with respect to the intraocular lens 4 disposed on the lens disposing part 15 is called "down", and a side opposite to the disposing-part bottom face 25 side with respect to the intraocular lens 4 disposed on the lens disposing part 15 is called "up".

Figure 3A:
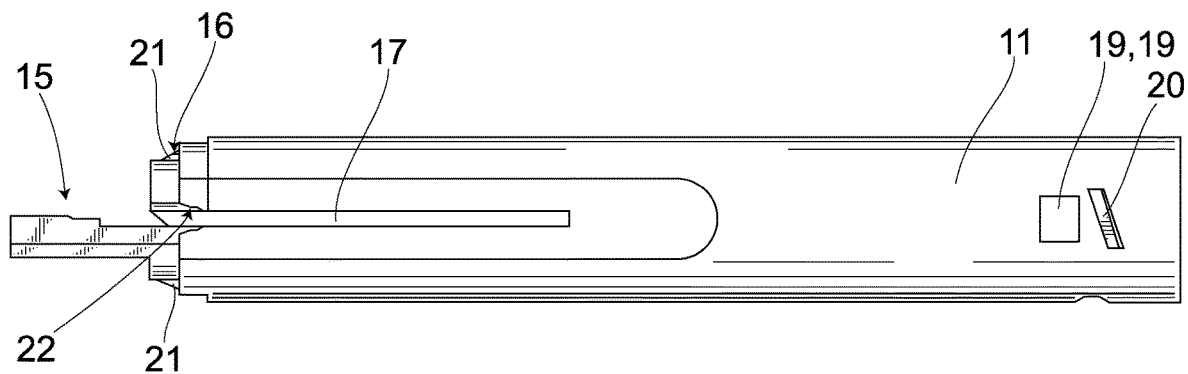
FIG. 3A is a side view showing the structure of a basal end member of the intraocular lens insertion device and FIG. 3B is a cross-sectional view thereof.
Figure 3B:
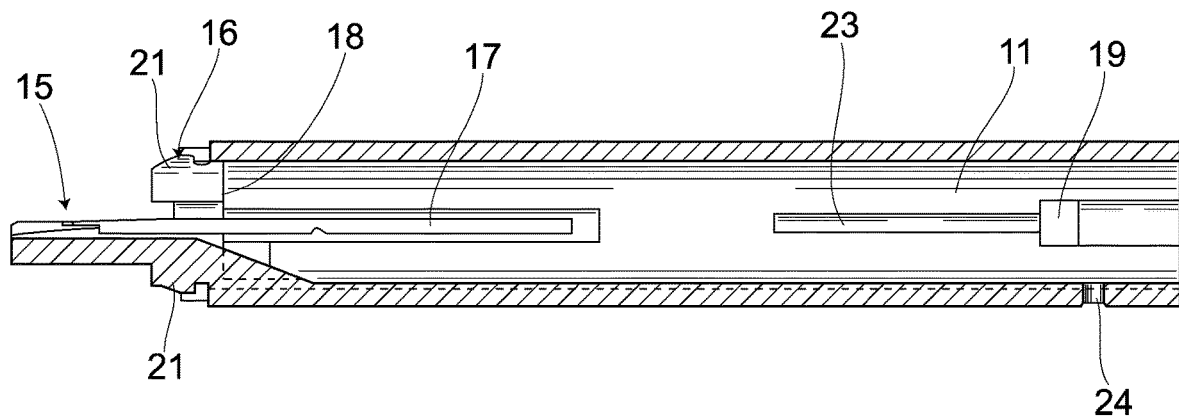

As shown in FIGS. 3A and 3B, the engagement member 16 has first protrusions 21, 21 and widened-part receivers 22, and the first protrusions 21, 21 and the widened-part receivers 22 are provided at the front end of the basal member 11. The two first protrusions 21, 21 are provided in a protruding manner on the outer faces of side walls in a direction orthogonal to the lens traveling axis A. The first protrusions 21, 21 are each formed in a shape like a wedge tapered toward the front. The two widened-part receivers 22 are provided on side walls in a direction orthogonal to the lens traveling axis A and to the direction in which the first protrusions 21, 21 are provided. The widened-part receiver 22 is formed by cutting out the side walls of the basal end member 11 so as to be widened toward the front. Accordingly, the first protrusions 21, 21 are provided in a direction orthogonal to the widened-part receivers 22.

The slider guides 17 comprise a pair of slits which are formed through the cylindrical side walls and are parallel to the lens traveling axis A. The slider guide 17 is so formed as to start from the front end of the basal end member 11 and to end at the approximate center thereof. The slider guide 17 has the widened-part receiver 22 formed at one end.

The basal end member 11 has the stopper 18 formed on the internal surface of the side wall thereof. The stopper 18 comprises a wall so formed as to plug up a portion of the internal surface of the basal end member 11 at the front end side.

The first latching openings 19 are provided at the other end side which is the rear end side of the basal end member 11, and the two first latching openings 19 are formed in the side walls in the direction orthogonal to the lens traveling axis A. The first latching opening 19 is integrally formed with a latching-part guide 23. The latching-part guide 23 is provided in the internal surface of the side wall, and is constituted by a groove having a bottom surface and extending toward the front in parallel with the lens traveling axis A.

The engagement protrusion 20 comprises a part of a thread constituting a male screw formed in such a way that the external surface of the side wall of the basal end member 11 functions as a root of the thread, and is provided on the external surface of the side wall in a direction orthogonal to the lens traveling axis A. The side wall is provided with a second latching opening 24.

Figure 5A:
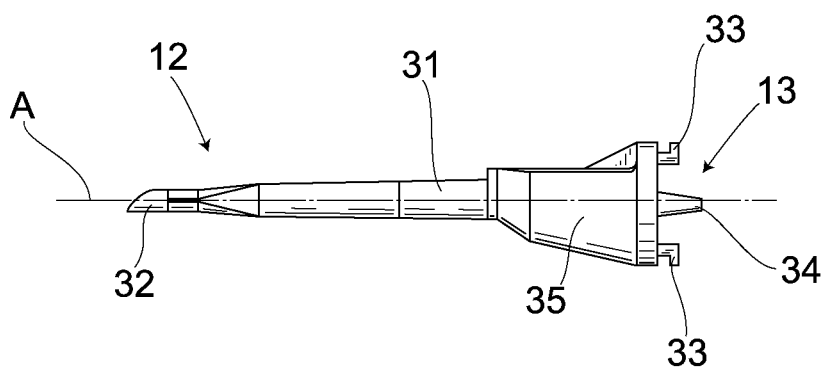
FIG. 5A is a side view showing the structure of a leading end member.
Figure 5B:
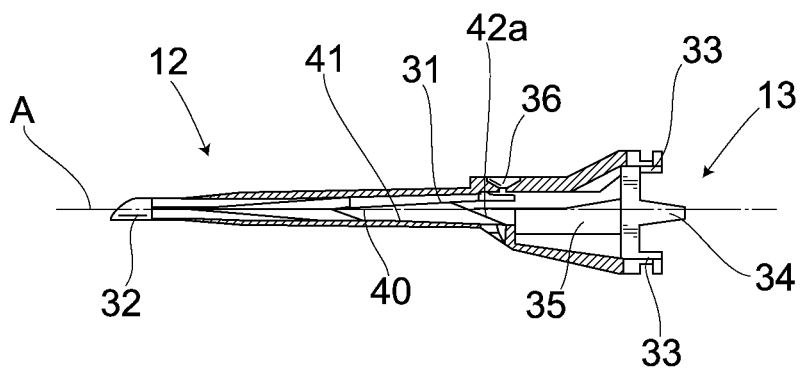
FIG. 5B is a cross-sectional view thereof.

As shown in FIGS. 5A, 5B and 30, the leading end member 12 has the first coupler 13, a transition part 31, and a nozzle 32, and folds up the intraocular lens pushed out from the main body compactly, and ejects out the intraocular lens 4 from the nozzle 32 at the leading end. The leading end member 13 has the first coupler 13 formed at the outer edge of the basal end, and coupled to the main body 6. The leading end member 13 further has the transition part 31 and the nozzle 32 in this order toward the front along the lens traveling axis A.

The first coupler 13 has engagement receivers 33, 33, a widened part 34, and a protective part 35, and couples the leading end member 12 and the main body 6 together. The engagement receivers 33, 33 comprise a pair of openings formed in the base end of the leading end member 12. The opening that constitutes the engagement receiver 33 is formed in a rectangular shape, and is formed in such a manner as to run in a direction orthogonal to the lens traveling axis A.

The widened part 34 is provided on the base end of the leading member 12 orthogonal to the direction in which the engagement receivers 33, 33 are formed, in a protruding manner. The widened part 34 comprises a protrusive piece each formed in a shape like a wedge tapered toward the rear from the base end.

The protective part 35 is provided between the base end of the leading end member 12 and the transition part 31, and is so formed as to cover the exterior of the lens disposing part 15.

Figure 6:
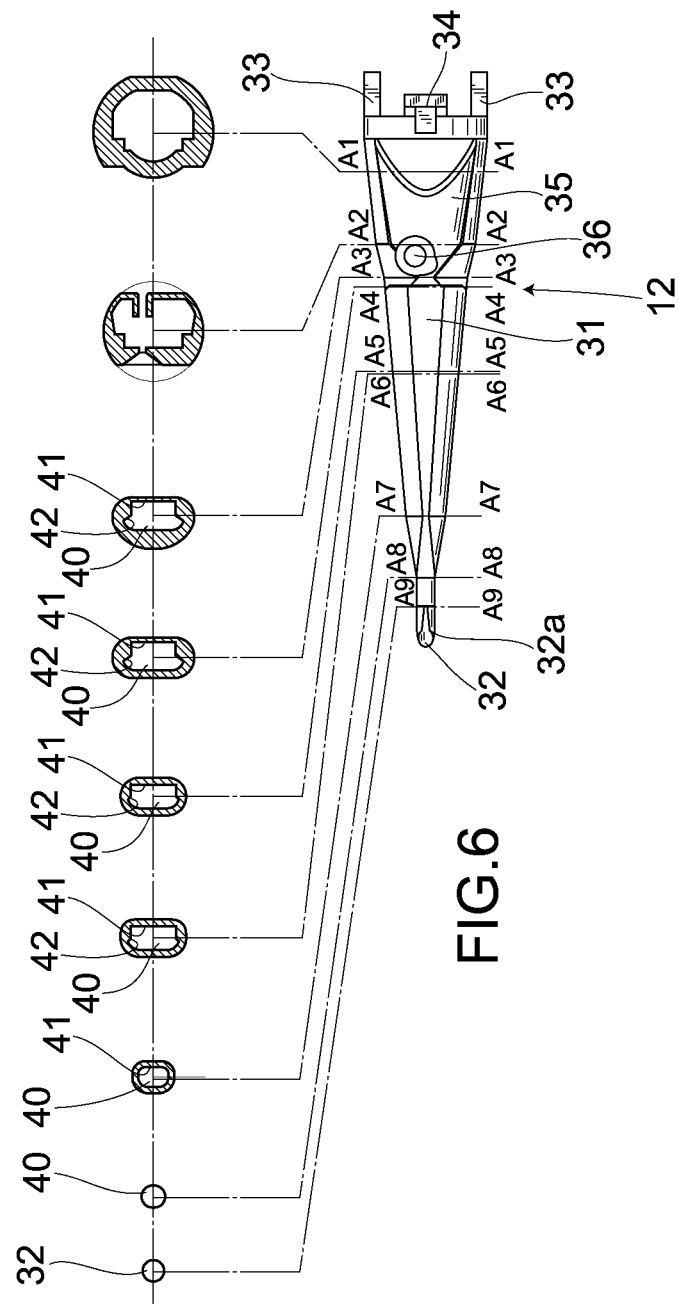
FIG. 6 is a top plan view showing the structure of a transition part with vertical cross-sectional views taken therethrough.

As shown in FIG. 6, the transition part 31 has a lumen 40, a transition-part bottom face 41, and a leading end rail 42 serving as a rail, and folds the intraocular lens 4 disposed on the lens disposing part 15 in a predetermined shape while moving the intraocular lens 4. Note that the rail is so formed as to support portions of an outer edge 4c of the intraocular lens 4, parallel to the lens traveling axis A, from beneath.

The lumen 40 is formed in a shape like a mortar tapered toward the leading end from the base end. The lumen 40 has the transition-part bottom face 41 and the leading end rail 42 at the bottom thereof.

The transition-part bottom face 41 comprises a tabular member formed horizontally around the lens traveling axis A. The transition-part bottom face 41 is connected to the leading end of a disposing-part bottom face 25 of the basal end member 11, which is the front end thereof, at the basal end of the leading end member 12, which is the rear end thereof. The transition-part bottom face 41 converges into the lumen 40 at the leading end, which is the front end of the leading end member 12.

The leading end rail 42 is formed by causing both sides of the transition-part bottom face 41 to protrude upwardly from the transition-part bottom face 41. The base end which is the rear of the leading end rail 42 matches a part where the protective part 35 and the transition part 31 are connected together. Accordingly, the base end which is the rear end of the leading end rail 42 is connected to the leading ends, which are the front ends of the base end rails 28, 28 provided on the basal end member 11. The leading end rail 42 has an inclined face 42a which inclines upwardly toward the front. The inclined face 42a is formed in the vicinity of the base end of the lumen 40 formed in a shape like a mortar tapered toward the leading end from the base end. The inclined face 42a has a rear base end which holds the intraocular lens 4 in such a way that a portion near the center of the optical part of the intraocular lens 4 does not contact the transition-part bottom face 41, and has a front leading end which has an inclination becoming equal to the height of the center of the height of the lumen 40. Further, the leading end of the inclined face 42a is connected to a parallel plane, and converges gently into the lumen 40 toward the front leading end of the leading end member 12.

The transition part 31 structured as mentioned above has the leading end communicated with the nozzle 32. The nozzle 32 has a circular cross section, and has a leading end formed in a shape inclined downwardly toward the front, and has a slit 32a formed on the top.

Note that the leading end of the inclined face 42a may have a height increased as it converges into the lumen 40 toward the front end without being connected to the parallel plane.

The inclined face 42a of the leading end rail 42 has a certain inclination angle to the transition-part bottom face 41 in FIG. 6, but may be parallel to the transition-part bottom face 41, and in this case, it is desirable that the inclined face 42a should have a height approximately same as that of the base end rail 28 in the vicinity of the basal end member 11, and should gradually increase the height toward the front. The leading end rail 42 may employ a structure of gradually increasing the inclination angle toward the leading end, i.e., having a height approximately equal to that of the base end rail 28 in the vicinity of the basal end member 11, and of gradually inclining inwardly toward the leading end.

The protective part 35 has a through hole 36 opened in a direction orthogonal to the lens traveling axis A and the transition-part bottom face 41. The through hole 36 is provided at that portion where the leading end of the lens disposing part 15 contacts when the basal end member 11 is assembled with the leading end member 12.

(b) Slider

As shown in FIGS. 7A and 7B, the slider 7 has a lens control mechanism 45 and a lock mechanism 46. The lock mechanism 46 prevents the plunger 8 from moving accidentally, and the lens control mechanism 45 moves and deforms the intraocular lens 4 disposed on the lens disposing part 15 as a first stage of a movement and a deformation.

The lens control mechanism 45 has a lens push-out part 47, a guide groove 48, wings 49, 49, operation parts 50, 50, a loop guide 51, a lens holder 52 and a stopper piece 53.

The lens push-out part 47 is constituted by a part of a circular arc having such a curvature radius as to define an approximately same contour as that of the lens, and is so formed as to contact the intraocular lens 4 surface by surface.

The guide groove 48 is formed in such a way that the plunger 8 can move back and forth along the lens traveling axis A, and the leading end of the plunger 8 can protrude frontward from the lens push-out part 47. The guide groove 48 is constituted by a groove which is formed through a one side face of the slider 7 and is parallel to the lens traveling axis A.

The wings 49, 49 are provided on both side faces of the slider 7 across the lens traveling axis A in a protruding manner so as to engage with the slider guides 17. The wings 49, 49 each have the operation part 50, 50 provided integral with the respective protruding ends thereof. The operation parts 50, 50 are each formed of a tabular member parallel to the lens traveling axis A, and each have a plurality of grooves 55 formed on the external surface in a direction orthogonal to the lens traveling axis A.

The stopper piece 53 is constituted by a wall protruding in a direction orthogonal to the lens traveling axis A, and is provided on the other face side of the slider 7.

The loop guide 51 is formed on the other face side of the leading end of the slider 7 where no guide groove 48 is formed, and is constituted by a groove formed in a planer shape similar to a loop part (to be discussed later) of the intraocular lens 4. The loop part is held in the internal part of the guide groove 48 in such a state that no stress is substantially applied thereto.

Figure 8:
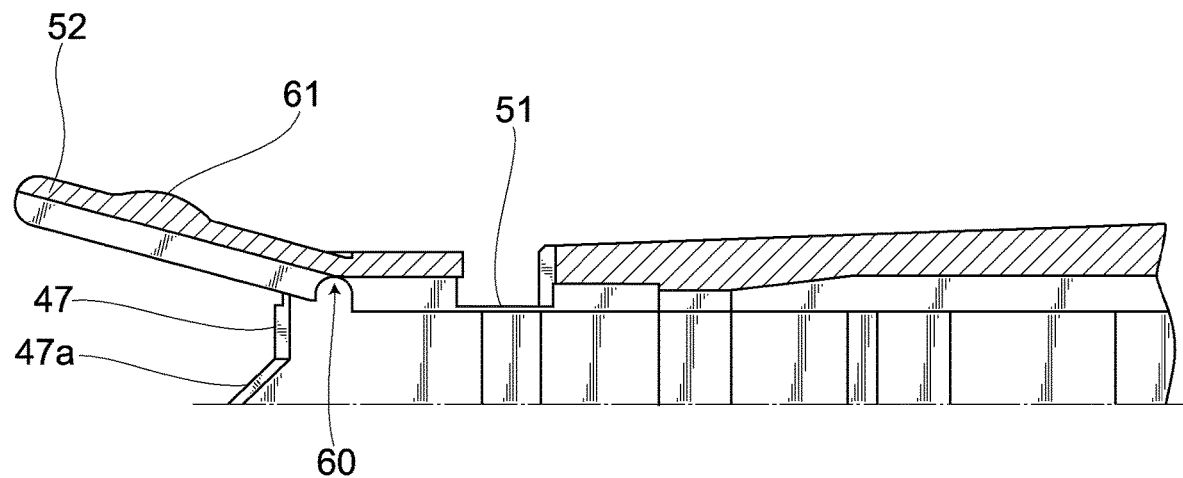
FIG. 8 is a partial enlarged view showing the slider.

As shown in FIG. 8, the lens holder 52 is provided above the lens push-out part 47 so that the lens holder 52 can tilt through a hinge 60. The lens holder 52 is constituted by a member formed in an approximately rectangular shape as viewed from the above, and has a sliding body 61 formed integral on the top face. The sliding body 61 is constituted by a member formed in a shape like a wagon roof extending in a direction orthogonal to the lens traveling axis A, and has a curved face facing upward.

As shown in FIGS. 7A and 7B, the lock mechanism 46 has tilting parts 65, 65, latching parts 66, 66 and extending parts 67, 67. The lock mechanism 46 surely locks the plunger 8 when unused, and surely releases the locking when in use.

The tilting parts 65, 65 are a pair across the lens traveling axis A, and protrude from the respective rear ends of the wings 49, 49 backwardly. The tilting parts 65, 65 are so provided as to tilt on a plane formed by the lens traveling axis A and the tilting parts 65, 65.

Figure 9:
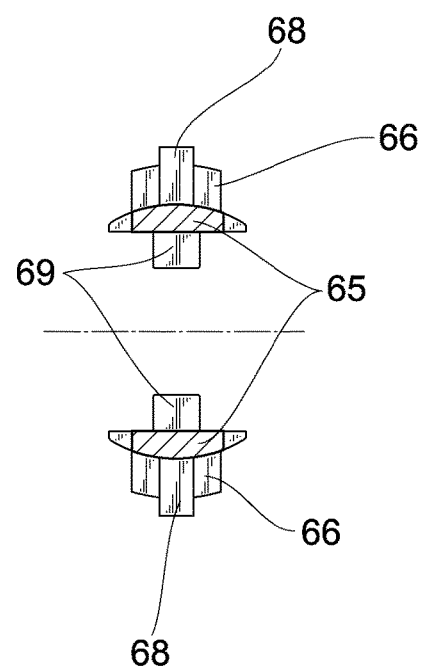
FIG. 9 is a cross-sectional view along a line A-A in FIG. 7.

The latching parts 66, 66 are formed at the respective center of the tilting parts 65, 65, and are each constituted by a protrusion protruding outwardly, i.e., in a direction away from the lens traveling axis A. The latching part 66 has a tiny protrusion 68 formed at the leading end protruding in the direction away from the lens traveling axis A (see, FIG. 9).

The extending parts 67, 67 are so formed as to protrude backwardly from the respective latching parts 66, 66, and each of which has an urging piece 69 protruding in a direction coming close to the lens traveling axis A (see, FIG. 7A). The urging piece 69 has a connection face 69a inclined inwardly, i.e., inclined so as to come closer and closer from the front of the extending part 67 to the rear thereof. The connection face 69a is connected to a holding face 69b parallel to the lens traveling axis A at the rear of the extending part 67.

(C) Plunger

Figure 10:
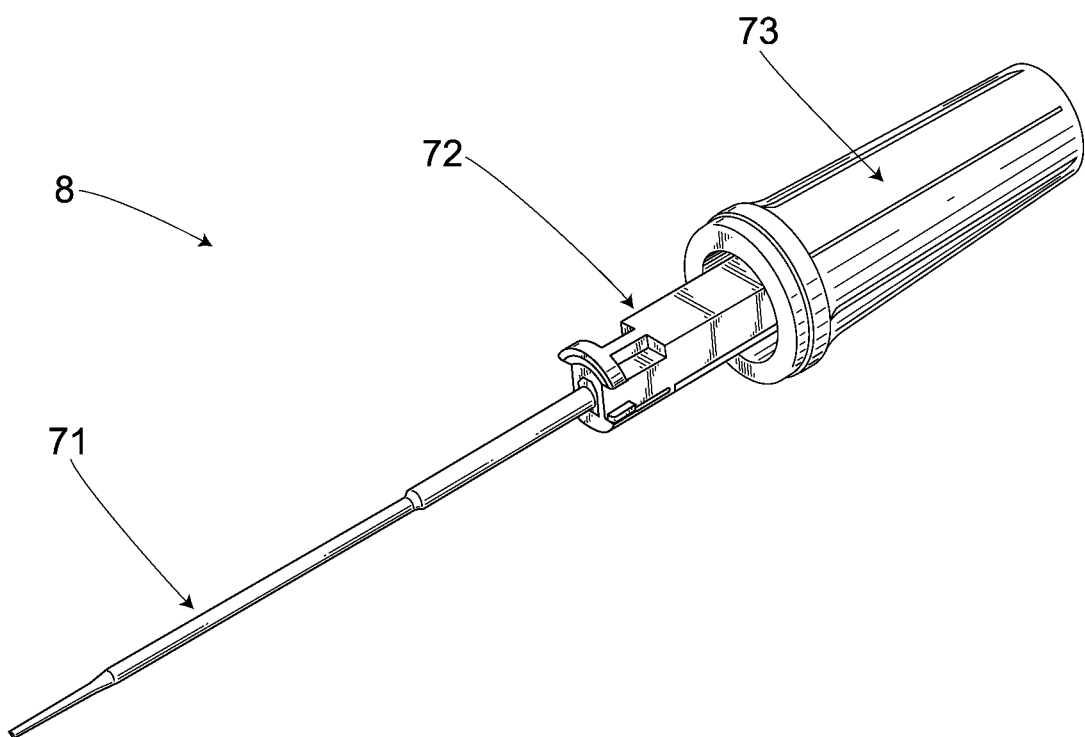
FIG. 10 is a perspective view showing the structure of the slider.

As shown in FIG. 10, the plunger 8 comprises a rod 71, a plunger main body 72, and a grip 73. The plunger 8 performs a second stage of a movement and a deformation on the intraocular lens 4 moved to some extent and deformed in a predetermined shape by the slider 7. The plunger 8 then inserts the intraocular lens 4 folded up compactly into an eye.

Figure 11:
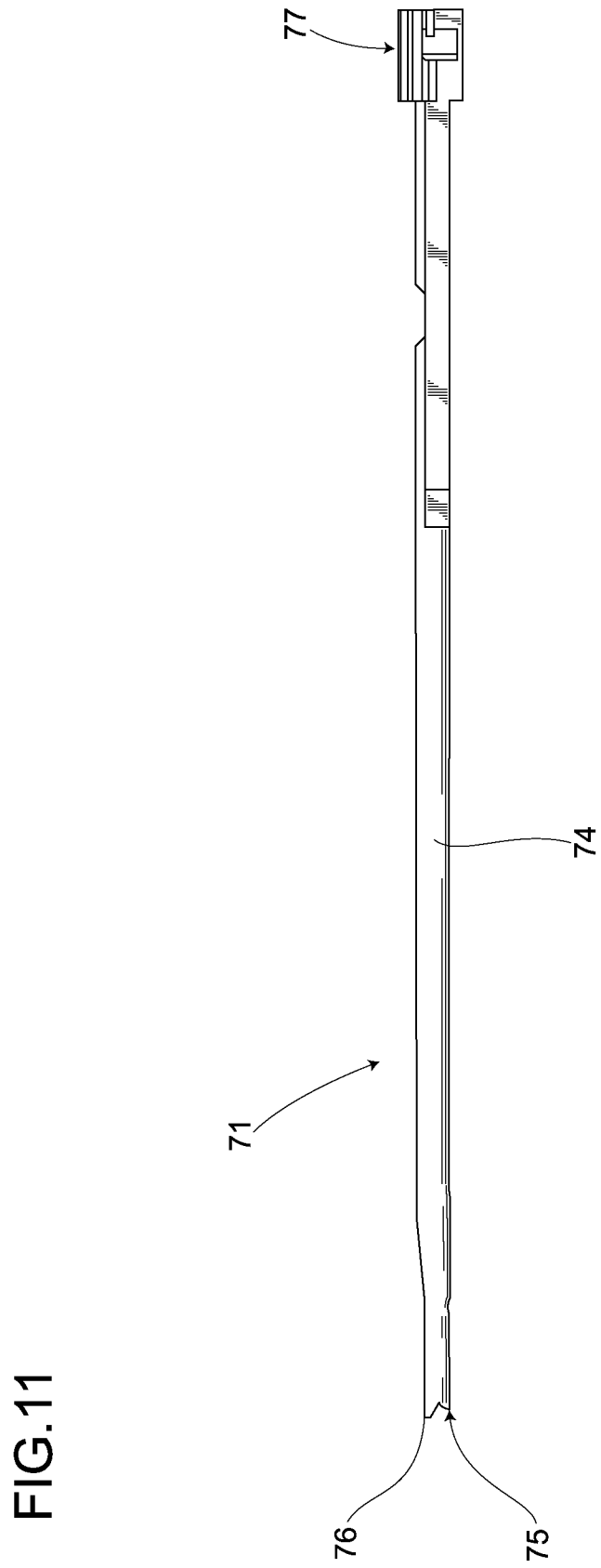
FIG. 11 is a front view showing the structure of a rod.

As shown in FIG. 11, the rod 71 has a rod-like axial part 74 formed in such a way that the one end thereof can protrude from the nozzle 32 of the leading end member 12, a lens contact part 75, a protrusive part 76 and a first attachment part 77.

The lens contact part 75 and the protrusive part 76 are provided at the one end of the rod 71, contact the outer edge 4c of the intraocular lens 4 that has undergone the first stage of a movement and a deformation by the slider 7, and perform the second stage of a movement and a deformation on the intraocular lens 4.

Figure 12A:
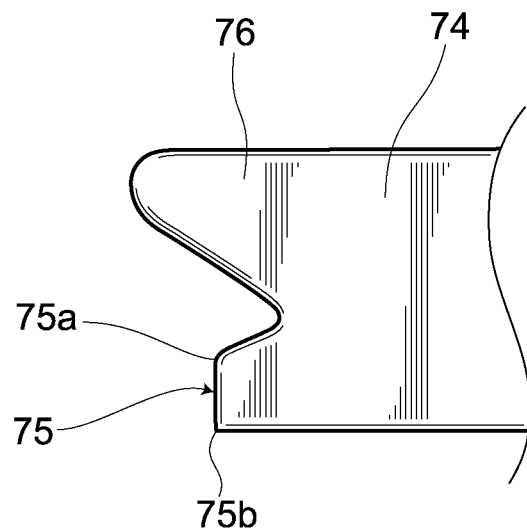
FIG. 12A is a partial enlarged view showing the rod and FIG. 12B is a partial enlarged view showing another rod.

As shown in FIG. 12A, the lens contact part 75 has a plane 75a formed at the front end of the rod 71 on the disposing-part bottom face 25 side. A one end corner 75b of the lens contact part 75, which is a part where the outer wall of the axial part 74 and the bottom portion of the lens contact part 75 are connected together, is formed in a shape like a letter R having a curvature radius less than or equal to 70% of the thickness of the outer edge 4c of the intraocular lens 4. It is further preferable that the curvature radius forming the one end corner 75b should be less than or equal to 50% of the thickness of the outer edge 4c of the intraocular lens 4. The plane 75a of the lens contact part 75 is so formed as to be vertical to the lens traveling axis A or formed in such a way that the upper end inclines backwardly with respect to the bottom end.

The protrusive part 76 is pressed in a direction orthogonal to the lens traveling axis A by the intraocular lens 4 pushed out and deformed by the plunger 8. Namely, the protrusive part 76 is so formed as to slide into the overlapped portion of the outer edge 4c of the intraocular lens 4 folded as it travels in the transition part 31. Accordingly, the protrusive part 76 is urged relatively by what corresponds to the thickness of the overlapped portion of the outer edge 4c of the intraocular lens 4. Therefore, as the intraocular lens 4 is deformed, the protrusive part 76 is pushed in a direction orthogonal to the lens traveling axis A, i.e., the central direction of the lumen 40 by the intraocular lens 4. The protrusive part 76 is provided on the other side of the front end of the rod 71, and protrudes frontward beyond the lens contact part 75. The protrusive part 76 has an upper face formed in a smooth convex curved face. In this manner, the rod 71 has the lens contact part 75 formed in a direction in which the protrusive part 76 is urged by the intraocular lens 4.

A recess, concaved rearwardly, is formed at the front end of the rod 71 between the lens contact part 75 and the protrusive part 76. This recess is provided to bend the protrusive part 76 when the lens contact part 75 is pushing the intraocular lens 4, and is able to absorb an excessive force applied from the protrusive part 76 to the outer edge 4c of the intraocular lens 4.

Figure 12B:
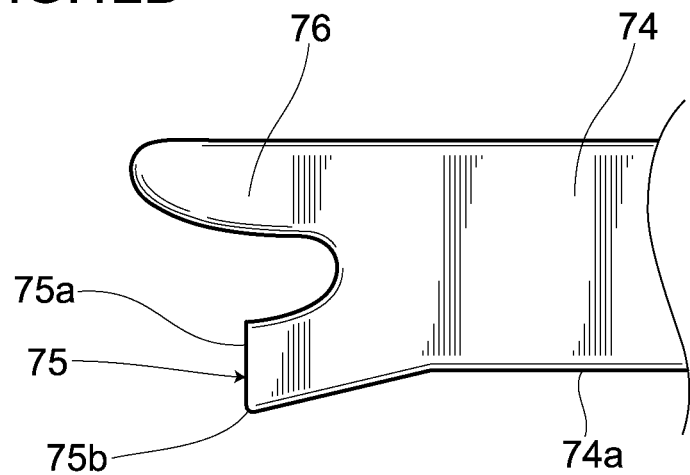

As shown in FIG. 12B, the lens contact part 75 may be formed in a shape such that at least a part thereof protrudes downwardly from the axial part 74. More specifically, a lower outer wall 74a of the axial part 74 gradually inclines downwardly toward the leading end, and the lens contact part 75 is provided at the leading end in a protruding manner.

Figure 13:
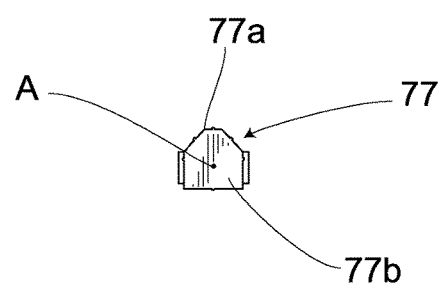
FIG. 13 is a right side view showing the rod.

The rod 71 has the first attachment part 77 provided at the other end of the rod 71 which is the rear end thereof. As shown in FIG. 13, the first attachment part 77 has a shape that one side of the cross section rises up, and the other end is flat. In this manner, the first attachment part 77 has an asymmetrical cross section in a direction orthogonal to the lens traveling axis A.

Figure 14A:
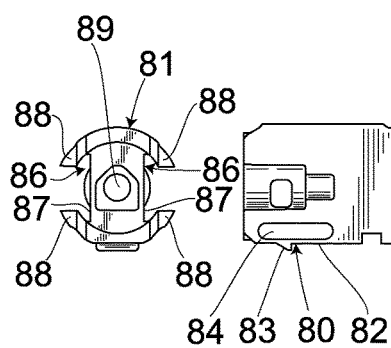
FIG. 14A is a front view showing the structure of a plunger and FIG. 14B is a left side view thereof.
Figure 14B:
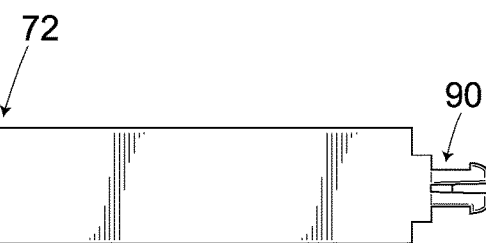

As shown in FIGS. 14A and 14B, the plunger main body 72 has a second latching part 80 and a circular disk part 81. The second latching part 80 is provided on the front outer face of the plunger main body 72, and is constituted by an elastic piece 82, and a protrusive piece 83 provided on the elastic piece 82. The elastic piece 82 forms a hollow 84 in the plunger 8, and comprises a thin tabular member laid across the face of the hollow 84 in a hanging manner.

The circular disk part 81 is formed in a coaxial circular shape with the central axis of the plunger main body 72, and has a pair of release grooves 86, 86 across that central axis. Each release groove 86 has a shape similar to the shape of the latching part 66 as viewed from the lens traveling axis A direction, and has a wide bottom face 87 provided in the vicinity of the central axis and second protrusions 88 so formed as to block the bottom face 87 and touch internally the outer edge of the circular disk part 81.

Further, the plunger main body 72 has a first attachment hole 89 formed in the front end thereof, and a second attachment part 90 formed in the rear end.

Figure 15A:
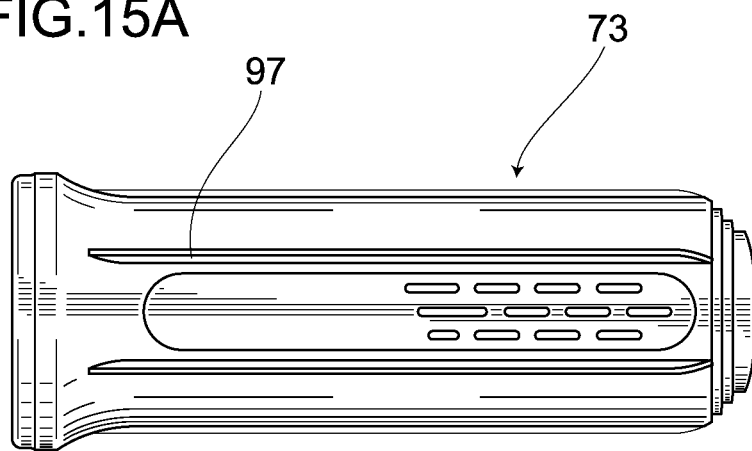
FIG. 15A is a side view showing the structure of a grip and FIG. 15B is a cross-sectional view thereof.
Figure 15B:
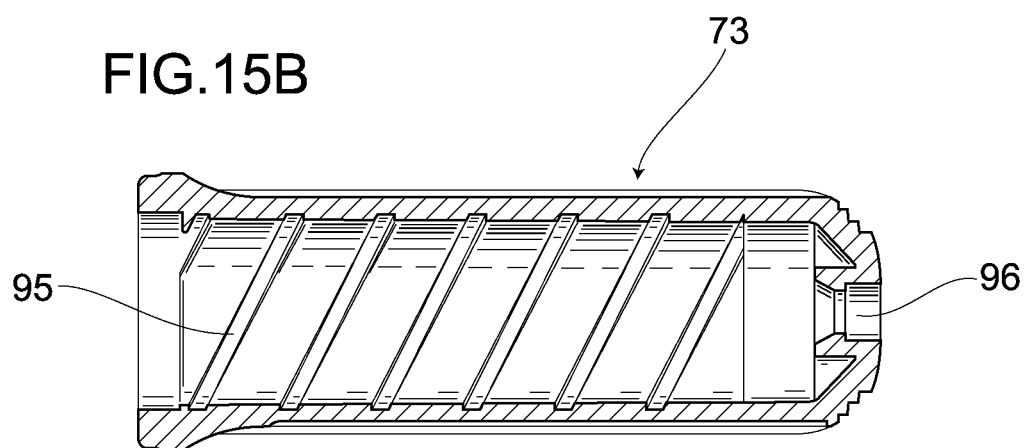

As shown in FIGS. 15A and 15B, the grip 73 is constituted by a member formed in a shape like a cylinder having a bottom. The grip 73 has an internal shape able to insert the basal end member 11 from the rear end thereof, and has a female screw 90 formed on the internal surface and threaded with the male screw formed on the outer face of the basal end member 11. The grip 73 has a second attachment hole 96 formed in the center of the bottom face thereof. The grip 73 further has a plurality of antislip protrusive strips 97 formed on the outer face thereof.

(2) Casing

Figure 16:
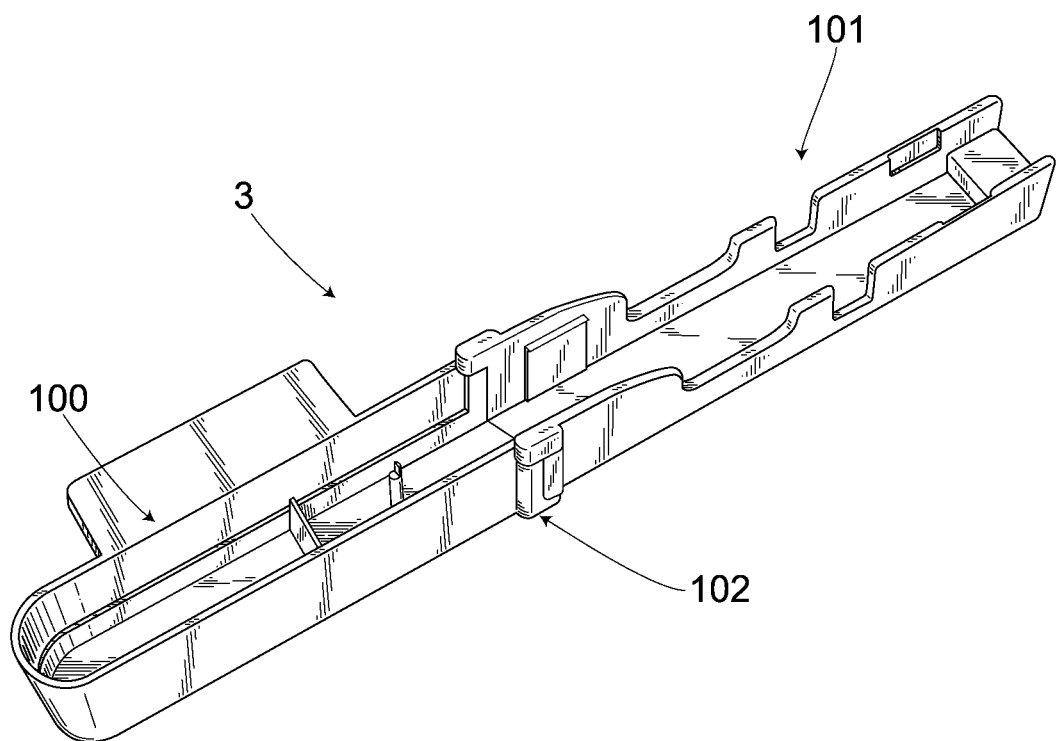
FIG. 16 is a perspective view showing the structure of a casing.

As shown in FIG. 16, the casing 3 is a lengthy box having an opened upper face and a flat bottom face 3a. The casing 3 comprises a case leading end part 100 and a case rear end part 101, both coupled together through a second coupler 102. The casing 3 protects the intraocular lens insertion unit 2 when unused, and holds the intraocular lens 4 disposed beforehand at a predetermined position.

Figure 17A:
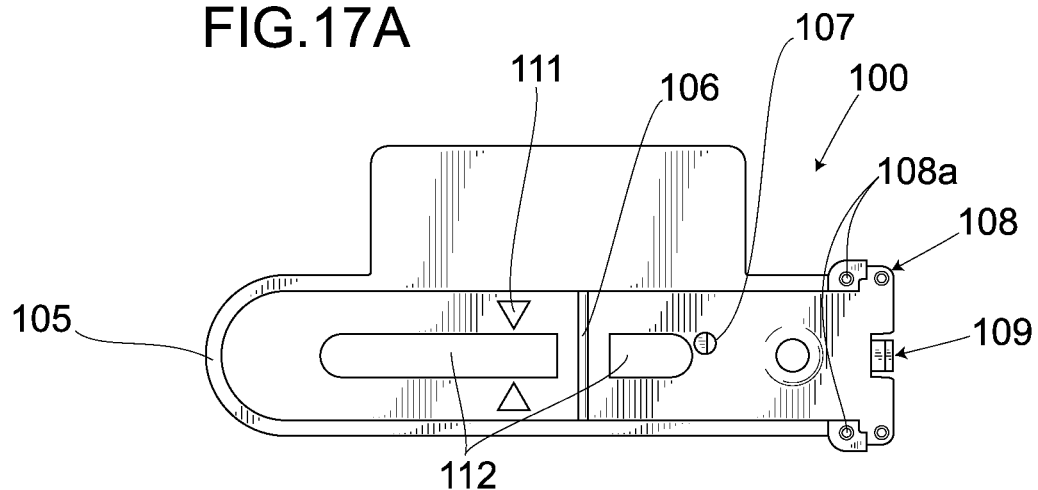
FIG. 17A is a plan view showing the structure of a case leading end.
Figure 17B:
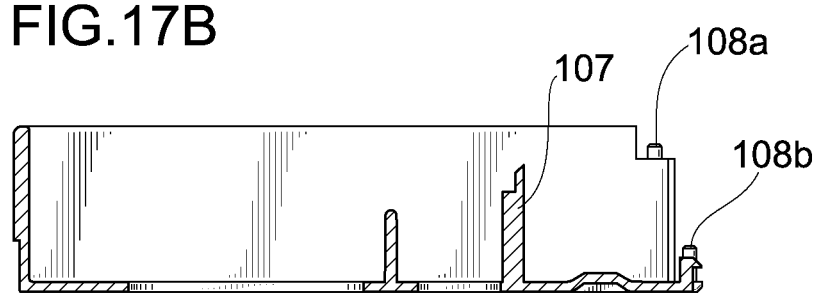
FIG. 17B is a vertical cross-sectional view thereof.
Figure 17C:
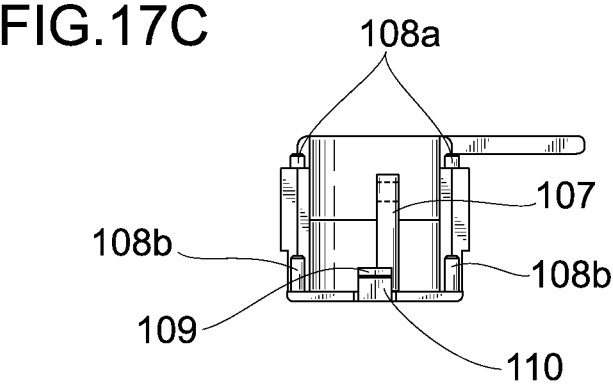
FIG. 17C is an end view thereof.

As shown in FIGS. 17A and 17B, the case leading end part 100 has a protective end 105, a reinforcement piece 106, a holding rod 107, latching rods 108, a latching claw 109, a marking 111, and a gas venting hole 112. The protective end 105 is a standing wall surrounding the one end of the case leading end part 100, and protects the nozzle 32 of the intraocular lens insertion unit 2 attached to the casing 3. The reinforcement piece 106 is a standing wall provided on the internal bottom face 3a of the casing 3, and increases the strength of the casing 3. The holding rod 107 is a cylindrical body provided on the internal bottom face 3a, and has an upper end formed in such a shape that a piece thereof on the protective end 105 side is half removed.

The latching rod 108 and the latching claw 109 are provided at the other end of the opened case leading end part 100. The latching rods 108 are a set of cylindrical bodies protruding in the vertical direction, and have upper latching rods 108a provided at both right and left upper portions of the other end of the case leading end part 100, and lower latching rods 108b provided at both right and left bottom portions of the other end of the case leading end part 100. The length of the lower latching rod 108b in the heightwise direction is longer than the length of the upper latching rod 108a in the heightwise direction. The upper latching rod 108a is formed at a position shifted to the one end side of the case leading end part 100 from the lower latching rod 108b.

The latching claw 109 is provided at a tabular member 110 protruding in the vertical direction from the casing bottom face 3a of the other end of the opened case leading end part 100. The tabular member 110 can elastically deform.

The marking 111 is provided at a position indicating a proper amount of a lubricant agent in filling the lubricant agent in the intraocular lens insertion unit 2 with the intraocular lens insertion unit 2 being placed in the casing 3. Note that the marking 111 can be marked on the intraocular lens insertion unit 2 itself, but the intraocular lens insertion unit 2 has a limited space for putting the marking 111, so that it is difficult to put a clear marking on the intraocular lens insertion unit 2. In a case where the marking 111 is put on the intraocular lens insertion unit 2, when the intraocular lens 4 is moved in the intraocular lens insertion unit 2, an operator cannot see the moving and deforming intraocular lens 4, thus reducing the operability for the operator. Therefore, it is not desirable to put the marking 111 on the intraocular lens insertion unit 2 itself.

On the other hand, according to the intraocular lens insertion device 1 of the embodiment, the marking 111 is put on the casing 3, so that an operator can clearly become aware of a position indicating the proper amount of the lubricant agent. Because the intraocular lens insertion unit 2 does not have the marking 111, the operator can see the moving and deforming intraocular lens 4 when the intraocular lens 4 moves in the intraocular lens insertion unit 2, thus improving the operability for the operator. The marking 111 can be in various forms, and for example, can be constituted by punch marking, printing, or a protrusive piece.

The gas venting hole 112 is formed in the base bottom face 3a, thus making it possible to smoothly introduce and remove a gas at the time of a gaseous sterilization.

Figure 18A:
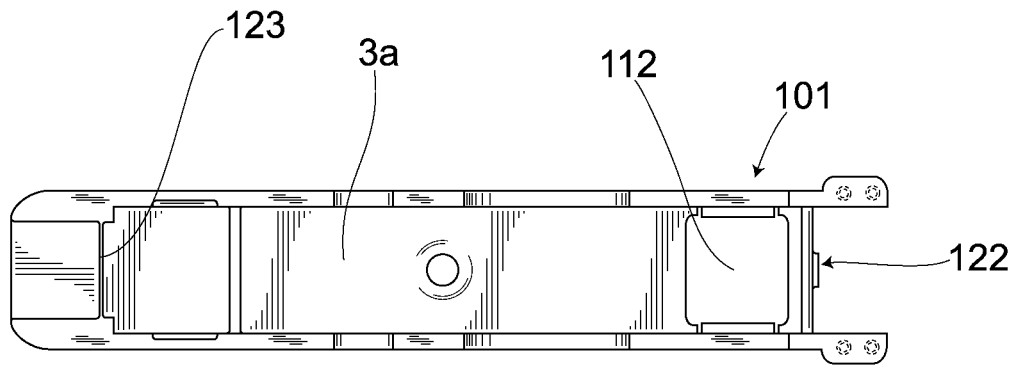
FIG. 18A is a plan view showing the structure of a case rear end.
Figure 18B:
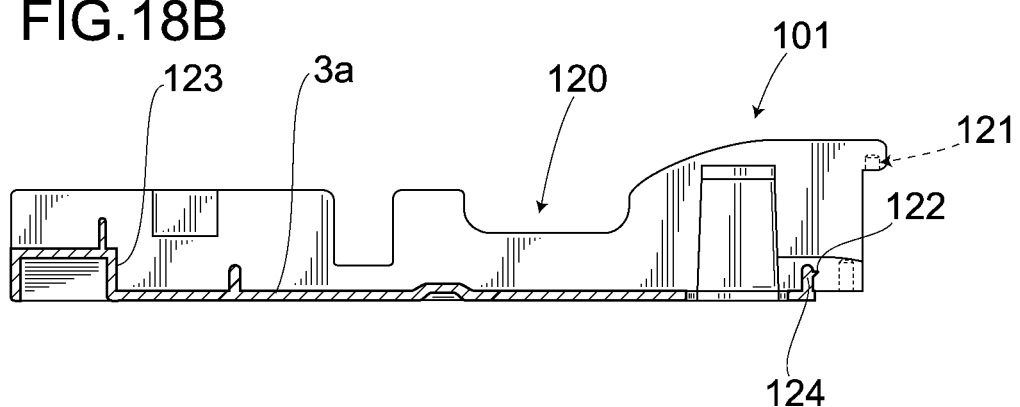
FIG. 18B is a vertical cross-sectional view thereof.
Figure 18C:
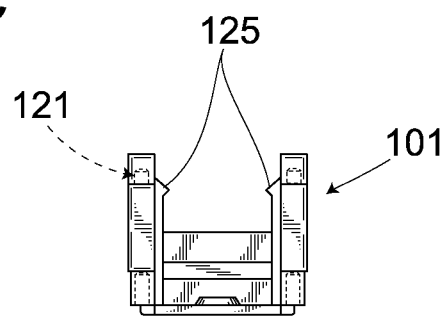
FIG. 18C is an end view thereof.

As shown in FIGS. 18A and 18B, the case rear end part 101 has a locking part 120, third latching holes 121, a claw receiving part 122, and a positioning part 123. The locking part 120 is formed by cutting both side walls so as to substantially correspond to the operation parts 50, 50. The third latching holes 121 are in positions, which are located at an opened end of the case rear end part 101, and correspond to the respective latching rods 108 formed on the case leading end part 100. The positioning part 123 is formed by raising the casing bottom face 3a of the other end of the case rear end part 101 in a vertical direction.

The claw receiving part 122 is provided at a tabular member 124 protruding from the casing bottom face 3a of the opened end of the case rear end part 101 in the vertical direction. The tabular member 124 can elastically deform.

The case rear end part 101 has detachment preventive parts 125 formed on the internal surfaces of the respective side walls. The detachment preventive part 125 has a protrusion protruding inwardly, and the upper end of the protrusion has a face inclined gently.

2. Assembling method

Next, an explanation will be given of the method of assembling the intraocular lens insertion device 1 of the invention with reference to the accompanying drawings.

Figure 19:
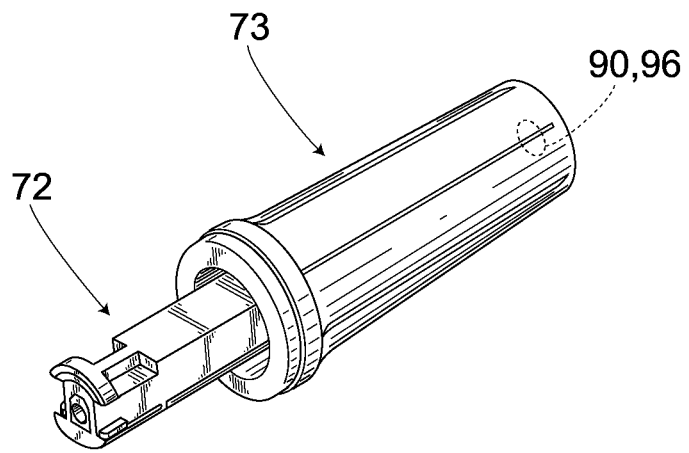
FIG. 19 is a perspective view showing an assembling method step by step.
Figure 20:
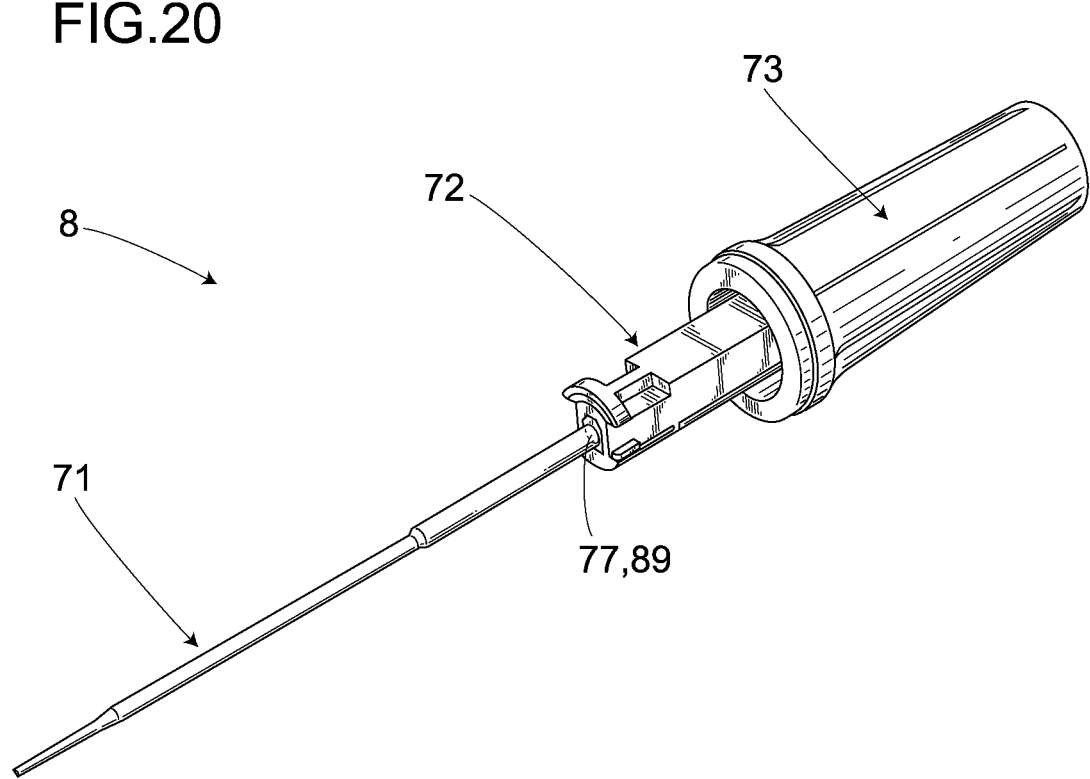
FIG. 20 is a perspective view showing the assembling method step by step.

First, the second attachment part 90 of the plunger main body 72 is fitted into the second attachment hole 96 of the grip 73, thereby coupling the grip 73 and the plunger main body 72 (see, FIG. 19). At this time, the second attachment part 90 is axially supported by the second attachment hole 96. Accordingly, the grip 73 is rotatably supported with respect to the plunger main body 72. Next, the first attachment part 77 of the rod 71 is inserted into the first attachment hole 89 of the plunger main body 72, and fixes the rod 71 to the plunger main body 72 (see, FIG. 20). Because the first attachment part 77 of the rod 71 has a cross section asymmetrical in a direction orthogonal to the lens traveling axis A, the rod 71 can be surely fixed to the plunger main body 72 in a predetermined direction. The grip 73, the plunger main body 72, and the rod 71 are coupled together in this manner, thereby assembling the plunger 8.

Figure 21:
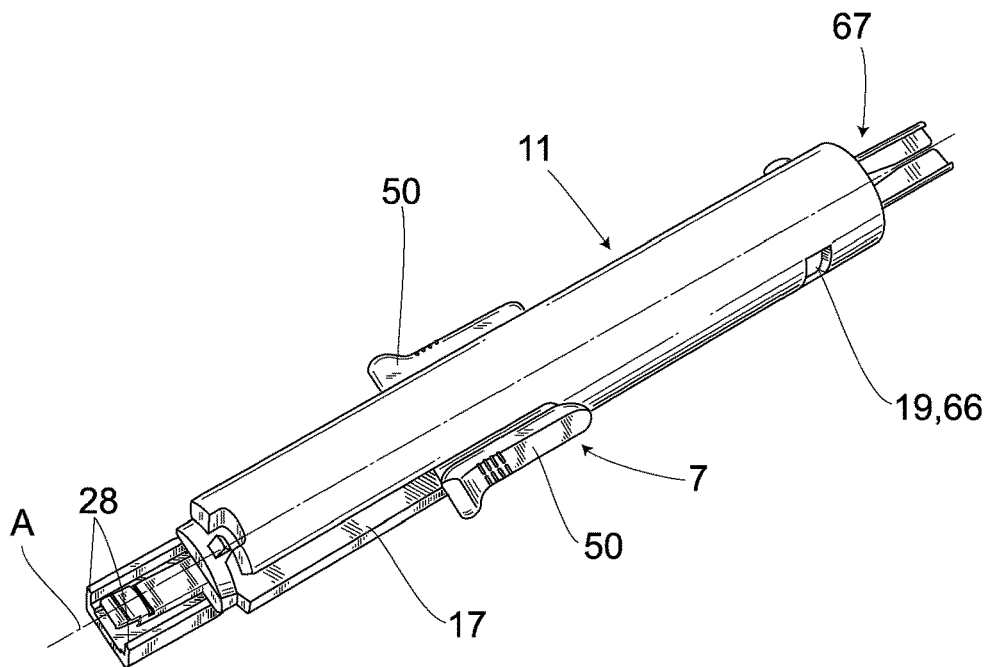
FIG. 21 is a perspective view showing the assembling method step by step.

Subsequently, the slider 7 is attached to the basal end member 11 (see, FIG. 21). To attach the slider 7 to the basal end member 11, one end of the basal end member 11 where the slider guide 17 is formed is widened in the direction orthogonal to the lens traveling axis A, and the extending parts 67, 67 are inserted through the one end to attach the slider 7. The slider 7 is attached in such a way that the direction thereof at this time becomes a direction in which the one end provided with the guide groove 48 faces the lens disposing part 15 of the basal end member 11. The wings 49, 49 are slid in the respective slider guides 17 by holding the operation parts 50, 50, and the slider 7 is slid until the wings 49, 49 reach the ends of the respective slider guides 17. At the same time, the latching parts 66, 66 of the slider 7 latch with the respective first latching holes 19 of the basal end member 11.

Figure 22:
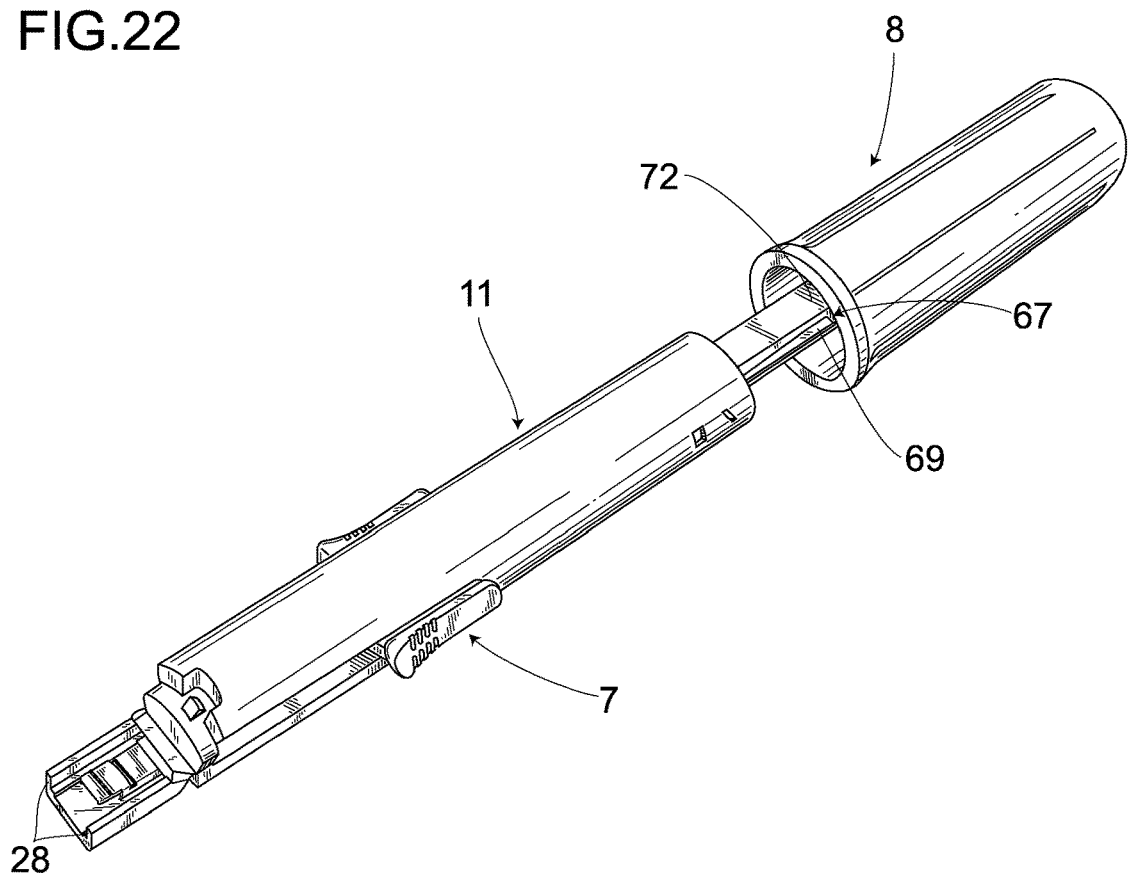
FIG. 22 is a perspective view showing the assembling method step by step.

The plunger 8 is inserted through the other end of the basal end member 11 to which the slider 7 is attached in this manner (see, FIG. 22). At this time, the rod 71 of the plunger 8 is first inserted, and the urging piece 69 of the slider 7 is caused to engage with the release groove 86 formed in the side face of the plunger main body 72. The plunger 8 is inserted until the second latching part 80 of the plunger main body 72 engages with the second latching hole 24 of the basal end member 11.

As explained above, the second latching part 80 is constituted by the elastic piece 82, and the protrusive piece 83 provided on the elastic piece 82, and the elastic piece 82 is a thin tabular member laid across the face of a hollow 84 formed in the plunger 8 in a hanging manner, thus being able to easily deform. Accordingly, by merely inserting the plunger 8 into the basal end member 11, the second latching part 80 can engage with the second latching hole 24, thereby facilitating an assembling of the plunger 8 to the leading end member 12.

The urging piece 69 inclines inwardly from the front of the extending part 67 to the rear thereof, i.e., inclines as to come close to the lens traveling axis A, so that as the plunger 8 engages with the guide groove 48, the tilting parts 65, 65 tilt outwardly. As the tilting parts 65, 65 tilt outwardly, the latching parts 66, 66 are urged outwardly, so that the latching parts 66, 66 can be surely engaged with the latching holes of the basal end member 11.

A frontward movement of the plunger 8 is locked because the second protrusions 88 of the circular disk part 81 contact the latching parts 66, 66 of the slider 7.

Figure 23:
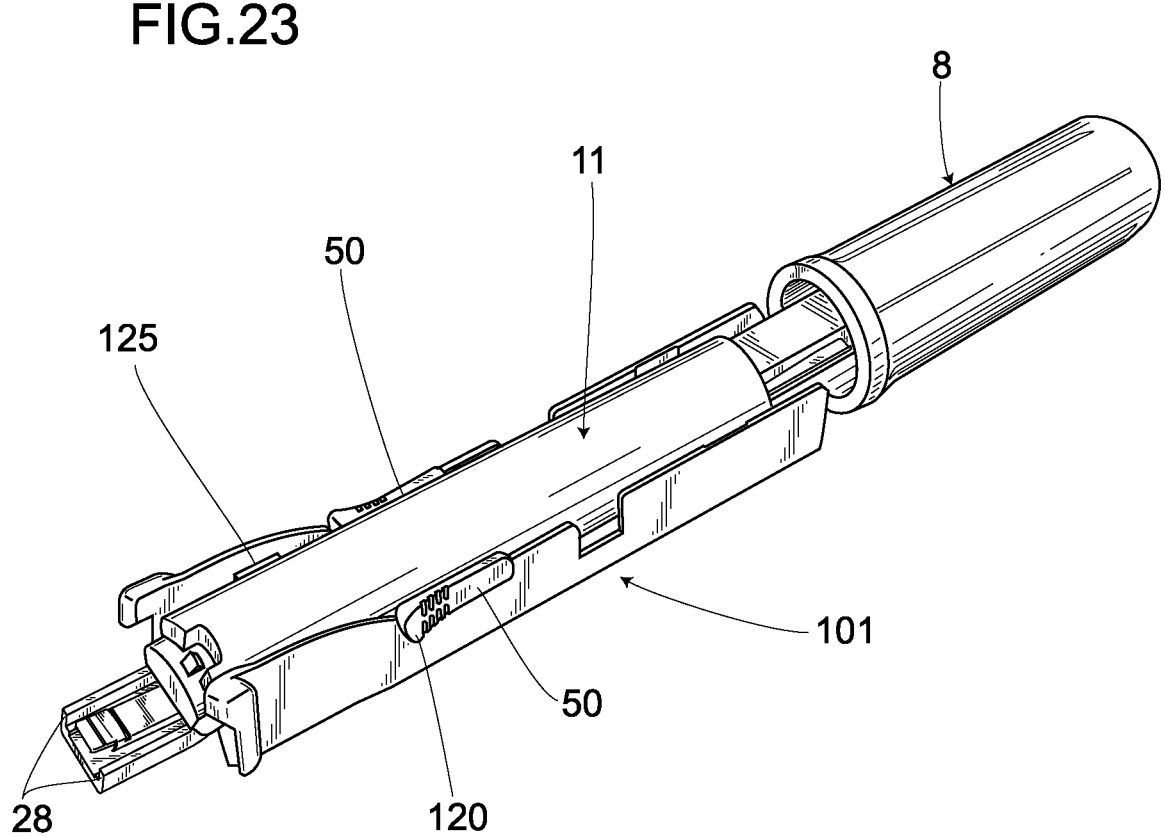
FIG. 23 is a perspective view showing the assembling method step by step.

With the frontward movement of the plunger 8 being locked, the basal end member 11 is placed in the case rear end part 101 (see, FIG. 23). The operation parts 50, 50 are inserted into the lock parts 120, and at the same time, the other end of the basal end member 11 contacts the positioning part 123 of the case rear end part 101. The outer face of the basal end member 11 is engaged with the detachment preventive parts 125 provided on both side walls of the case rear end part 101. The basal end member 11 is placed in the case rear end part 101 in this manner, and the operation parts 50, 50 of the slider 7 are inserted into the lock parts 120 provided in both side walls of the case rear end part 101, thereby locking a frontward or rearward movement of the slider 7.

Figure 24:
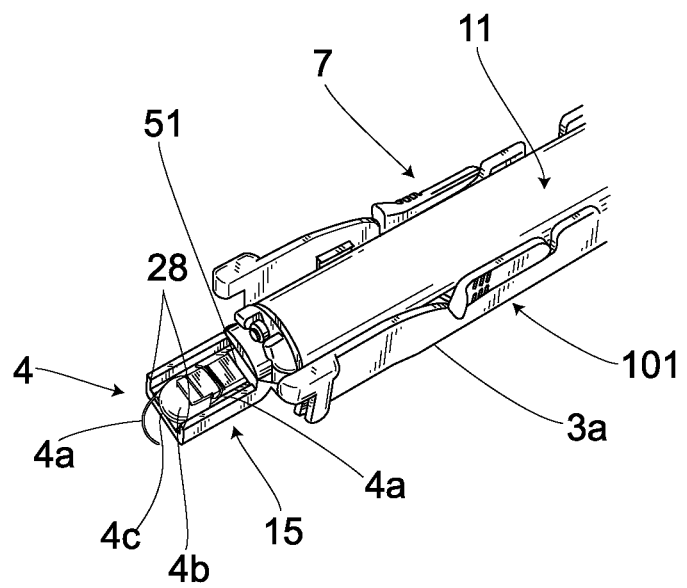
FIG. 24 is a perspective view showing the assembling method step by step.

With the plunger 8 and the slider 7 being locked in this manner, the intraocular lens 4 is disposed on the lens disposing part 15 (see, FIG. 24). The intraocular lens 4 is disposed in such a way that one of a pair of loop parts 4a is positioned at the groove of the loop guide 51 of the slider 7, and the outer edge 4c of the optical part 4b is mounted on the base end rails 28, 28 of the lens disposing part 15. Because the base end rails 28, 28 protrude upwardly from the disposing-part bottom face 25, the intraocular lens 4 can be disposed so as not to have the portion around the center of the optical part 4b contacted the disposing-part bottom face 25. Therefore, according to the intraocular lens insertion device 1, the intraocular lens 4 can be stored without applying a load to the intraocular lens 4.

According to the embodiment, the intraocular lens 4 is disposed with the basal end member 11 being placed in the case rear end part 101 having the flat casing bottom face 3a. Because the casing 3 is splittable, and one part thereof is attached to the basal end member 11, the basal end member 11 having the lens disposing part 15 can be held in a stable state without any specific jigs, thereby facilitating a disposition of the intraocular lens 4 on the lens disposing part 15.

Figure 25:
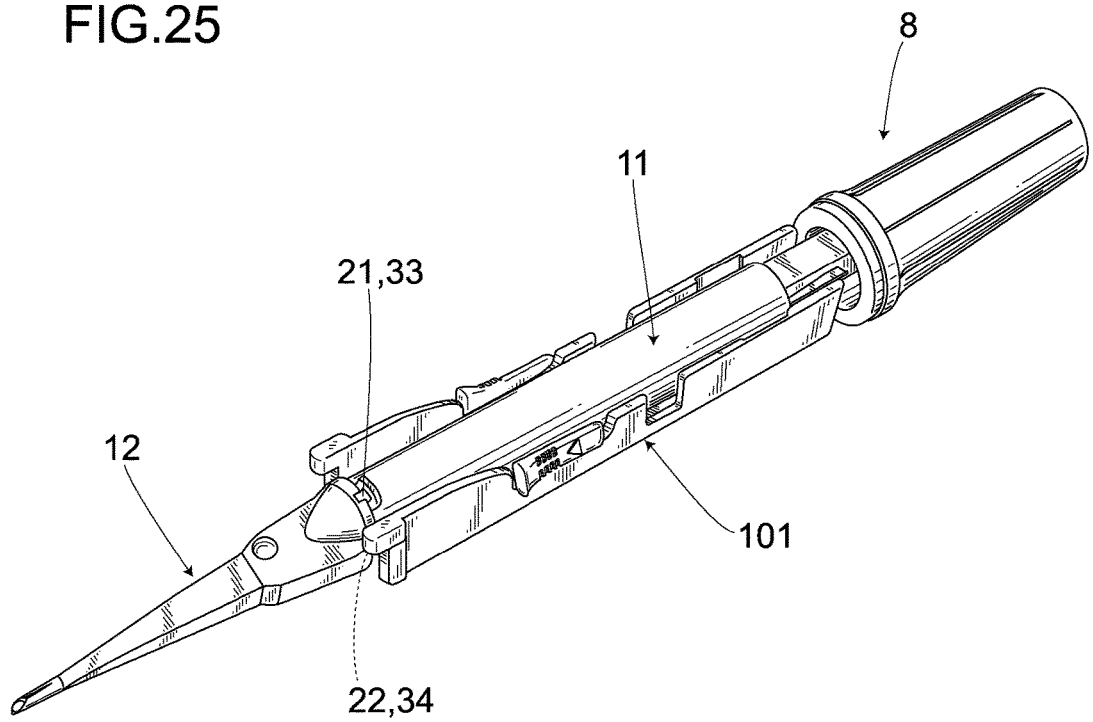
FIG. 25 is a perspective view showing the assembling method step by step.

The engagement part 16 of the basal end member 11 where the intraocular lens 4 is mounted is engaged with the engagement receivers 33, 33 of the leading end member 12, thereby coupling the leading end member 12 and the basal end member 11 together (see, FIG. 25). The leading end member 12 has the widened part 34, and as the widened part 34 is inserted into the widened-part receiver 22 of the basal end member 11, the one end of the basal end member 11 is pushed and widened in a direction orthogonal to the lens traveling axis A direction and the direction in which the widened-part receiver 22 is provided. Accordingly, the first protrusions 21, 21 of the basal end member 11 provided in a direction orthogonal to the widened-part receiver 22 are put into the engagement receivers 33, so that the basal end member 11 and the leading end member 12 can be surely coupled together.

By coupling the basal end member 11 and the leading end member 12 together, the disposing-part bottom face 25 of the basal end member 11 and the transition-part bottom face 41 of the leading end member 12 are connected together, and the base end rails 28, 28 of the basal end member 11 and the leading end rail 42 of the leading end member 12 are coupled together.

Because the leading end member 12 is provided with the protective part 35, the intraocular lens 4 disposed on the lens disposing part 15 can be protected.

Figure 26:
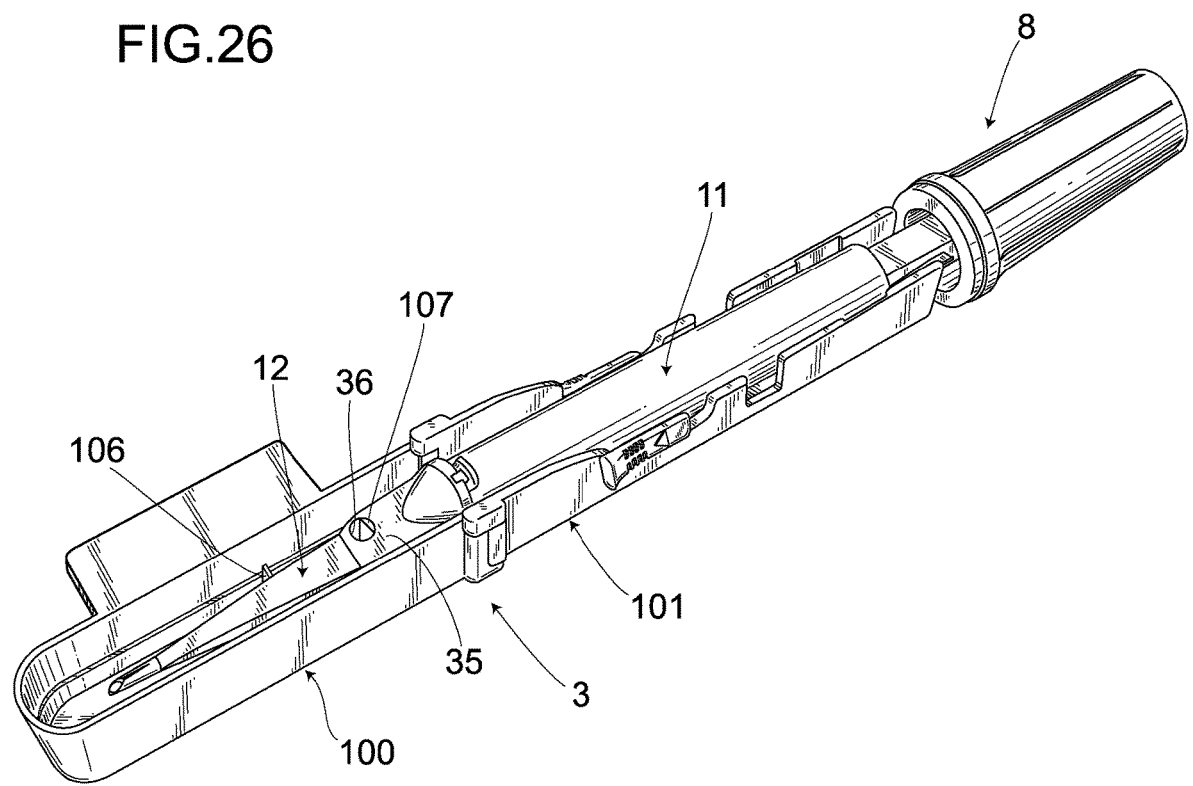
FIG. 26 is a perspective view showing the assembling method step by step.

Subsequently, the latching rod 108 of the case leading end part 100 is inserted into the third latching hole 121 of the case rear end part 101 to do positioning, and the latching claw 109 of the case leading end part 100 is engaged with the claw receiving part 122 of the case rear end part 101 (see, FIG. 26). Note that in a case where positioning is carried out with the four latching rods 108 like the embodiment, it is difficult to coincidentally position all four rods to the third latching holes 121.

Figure 27:
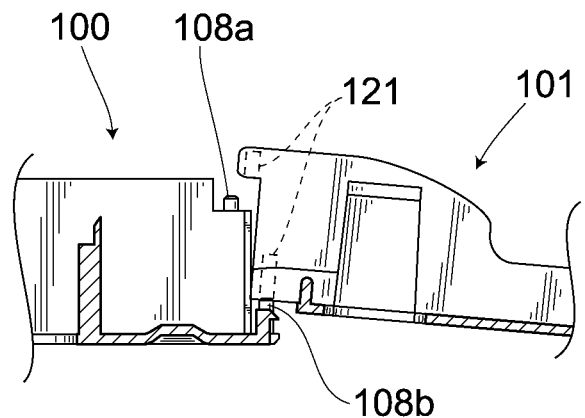
FIG. 27 is a partial cross-sectional view showing the way how the case leading end and the case rear end are coupled together.

On the other hand, according to the embodiment, the latching rod 108 at the case leading end part 100 is formed in such a way that the length of the lower latching rod 108b in the heightwise direction is longer than the length of the upper latching rod 108*a* in the heightwise direction. Accordingly, the lower latching rod 108*b* is first inserted into the third latching hole 121, and then the upper latching rod 108*a* is inserted into the third latching hole 121, thereby enabling a certain positioning. Namely, changing the lengths of the lower latching rod 108*b* and the upper latching rod 108*a* enables a positioning two positions by two positions, thereby facilitating positioning in comparison with a case like a conventional technology where positioning is carried out on four positions at the same time (see, FIG. 27).

According to the embodiment, because the latching claw 109 is engaged with the claw receiving part 122, the case rear end part 101 and the case leading end part 100 can be surely coupled together. Further, when the latching claw 109 is engaged with the claw receiving part 122, the latching claw 109 makes an engagement sound, thereby preventing an assembling failure like an improper engagement.

The case leading end part 100 has the holding rod 107 provided on the internal bottom face, and the holding rod 107 is inserted into the through hole 36 provided in the protective part 35 of the leading end member 12. The through hole 36 is provided in a position where the leading end of the lens disposing part 15 inserted in the protective part 35 abuts, so that the holding rod 107 prevents the intraocular lens 4 from moving frontward. Therefore, according to the embodiment, the intraocular lens 4 can be surely held at a predetermined position when carried.

3. Working and Effectiveness

Next, an explanation will be given of the working and effectiveness of the intraocular lens insertion device 1 of the embodiment.

First, with the intraocular lens insertion unit 2 being placed in the casing 3 (see, FIG. 26), a viscoelastic material as a lubricant agent is filled in the lens disposing part 15 of the intraocular lens insertion unit 2 through the through hole 36 provided in the leading end member 12.

Because the case leading end part 100 has the marking 111 provided at a position indicating the proper amount of the viscoelastic material, it is easy to fill the viscoelastic material at a proper amount.

According to the intraocular lens insertion device 1, with the intraocular lens insertion unit 2 being placed in the casing 3, the viscoelastic material is filled in the lens disposing part 15 in this manner, it is possible to fill the viscoelastic material with the slider 7 and the plunger 8 being locked and with the nozzle 32 being protected.

Note that the holding rod 107 provided on the case leading end part 100 is inserted into the through hole 36 to prevent the intraocular lens 4 from moving, but because the upper part of the holding rod 107 is formed in such a shape that a piece on the protective part 105 side is half removed, the through hole 36 on the upper part of the leading end member 12 is not plugged by the holding rod 107. Therefore, the viscoelastic material can be surely filled in the lens disposing part 15 through the through hole 36.

When the intraocular lens insertion unit 2 in which the viscoelastic material is filled is removed from the casing 3, the slider 7 becomes movable. Note that the plunger 8 is locked by the lock mechanism 9 so as not to move frontward.

Figure 28:
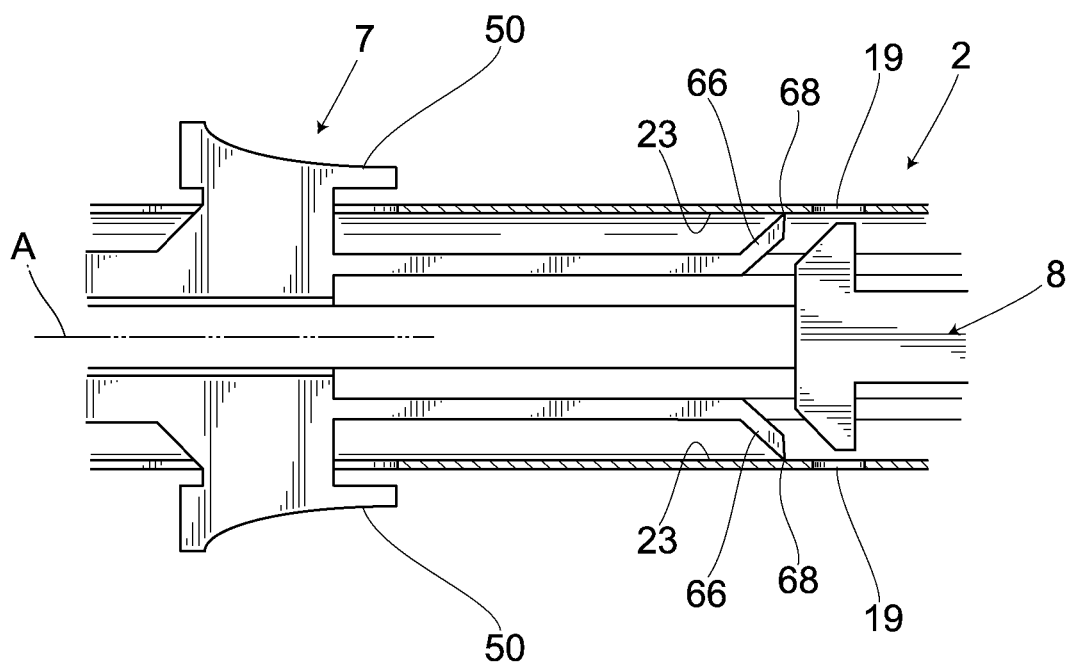
FIG. 28 is a partial cross-sectional view showing the way how the intraocular lens insertion device operates.

The operation parts 50, 50 are grasped, and the slider 7 is moved frontward. As the slider 7 is pushed out, the latching parts 66, 66 abut the internal edges of the first latching holes 19, 19, and the tilting parts 65, 65 tilt inwardly. As the slider 7 is further pushed out, the latching parts 66, 66 pass over the first latching holes 19, 19, and the tiny protrusions 68, 68 provided at the leading ends of the respective latching parts 66 engage with the latching-part guide 23. Then, the latching of the latching parts 66 and the first latching holes 19, 19 are released, so that the slider 7 can become movable frontward (see, FIG. 28).

Figure 29A:
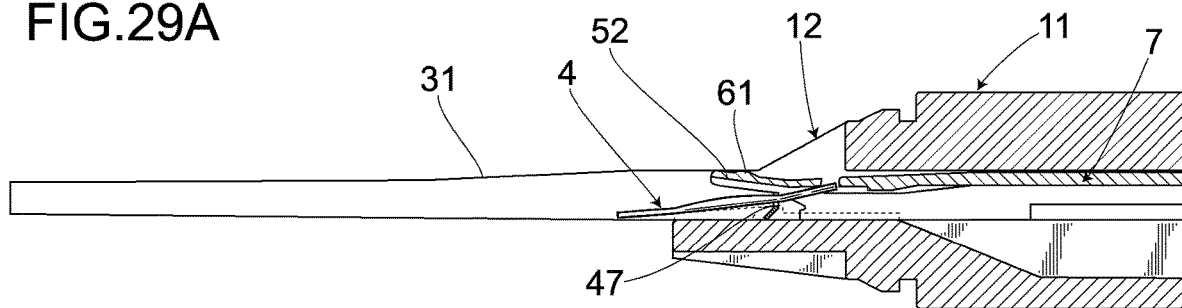
FIGS. 29A-29D are partial cross-section views showing the operation of the device step by step.
Figure 29B:
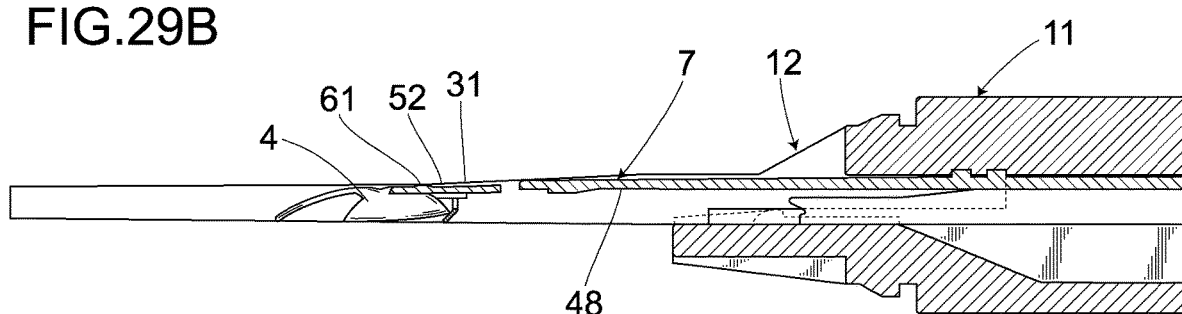

At the leading end of the slider 7, the first stage of movement and deformation are performed on the intraocular lens 4. That is, the lens push-out part 47 of the slider 7 abuts the outer edge 4*c* of the intraocular lens 4, and pushes out the intraocular lens 4 (see, FIG. 29A, FIG. 30A). At the same time, the lens holder 52 is pushed against the internal wall of the transition part 31, and swayed downwardly as viewed from a side, and pushes the one face of the optical part of the intraocular lens 4 in a downward direction, which is one direction (see, FIG. 29B, FIG. 30B).

On the other hand, the intraocular lens 4 moves on the leading end rail 42 that has the inclined face 42*a* inclined upwardly which is a direction opposite to the direction of pushing the intraocular lens 4 by the lens holder 52, as the intraocular lens 4 moves to the front.

Accordingly, the leading end rail 42 upwardly deforms both sides of the outer edge 4*c* across the lens traveling axis A as portions parallel to the lens traveling direction in the peripheral edge of the intraocular lens 4 in a direction opposite to the direction in which the intraocular lens 4 is pushed by the lens holder 52 (see, FIG. 30C).

Figure 29C:
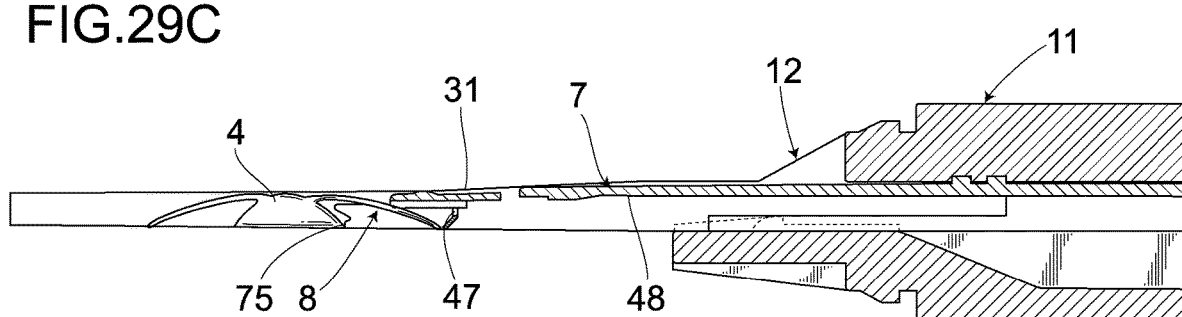

Therefore, according to the intraocular lens insertion unit 2 of the embodiment, the lens holder 52 pushes the optical part of the intraocular lens 4 downwardly, while the leading end rail 42 upwardly pushes both sides of the outer edge 4*c* of the intraocular lens 4 across the lens traveling axis A. Accordingly, the intraocular lens insertion unit 2 can surely fold the intraocular lens 4 in a predetermined shape, i.e., a shape that the optical part surely protrudes downwardly in the embodiment (see, FIG. 29C and FIG. 30D).

Note that according to the conventional intraocular lens insertion devices, the base end of the transition part is formed in an approximately diamond-like shape, and the leading end thereof is deformed into a circular shape gradually to deform an intraocular lens into a predetermined shape, the shape of the transition part is complex.

In contrast, according to the intraocular lens insertion unit 2 of the embodiment, the leading end rail 42 is provided with the inclined face 42*a* to deform both sides of the outer edge 4*c* of the intraocular lens 4 across the lens traveling axis A. Therefore, the shape of the transition part 31 is simplified, thus facilitating a manufacturing of the transition part.

Further, according to the intraocular lens insertion unit 2, the intraocular lens 4 is pushed out by the slider 7 having the lens push-out part 47 which has a larger contact face than the lens contact part 75 of the plunger 8. Accordingly, the intraocular lens insertion unit 2 can push out the intraocular lens 4 without applying local stress.

Still further, the sliding body 61 of the lens holder 52 is formed in a shape like a wagon roof, the sliding body 61 can slide uniformly against the internal wall of the transition part 31, so that it is possible to hold the optical part 4*b* of the intraocular lens 4 uniformly.

Figure 31:
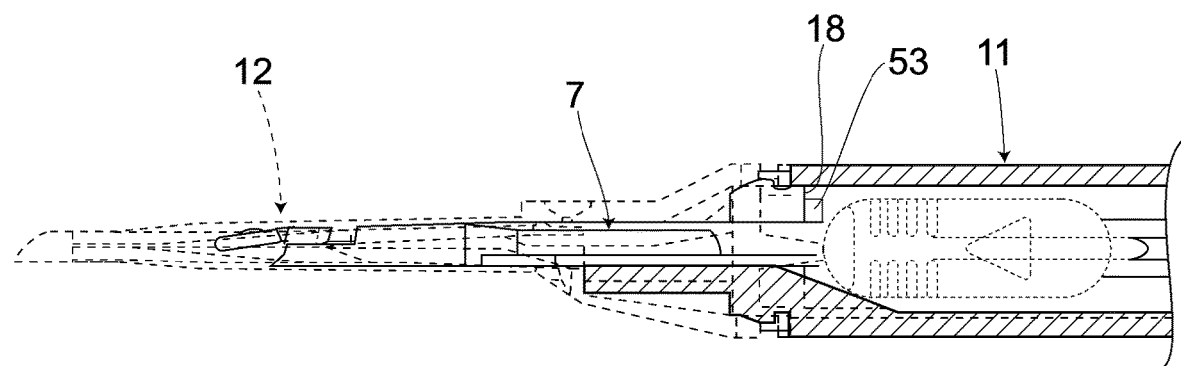
FIG. 31 is a partial cross-sectional view showing the operation.

Yet further, according to the intraocular lens insertion unit 2, because the stopper 18 which abuts the stopper piece 53 of the slider 7 is provided on the basal end member 11, even if the slider 7 is pushed out with strong force, the leading end member 12 does not come apart (see, FIG. 31).

Figure 32:
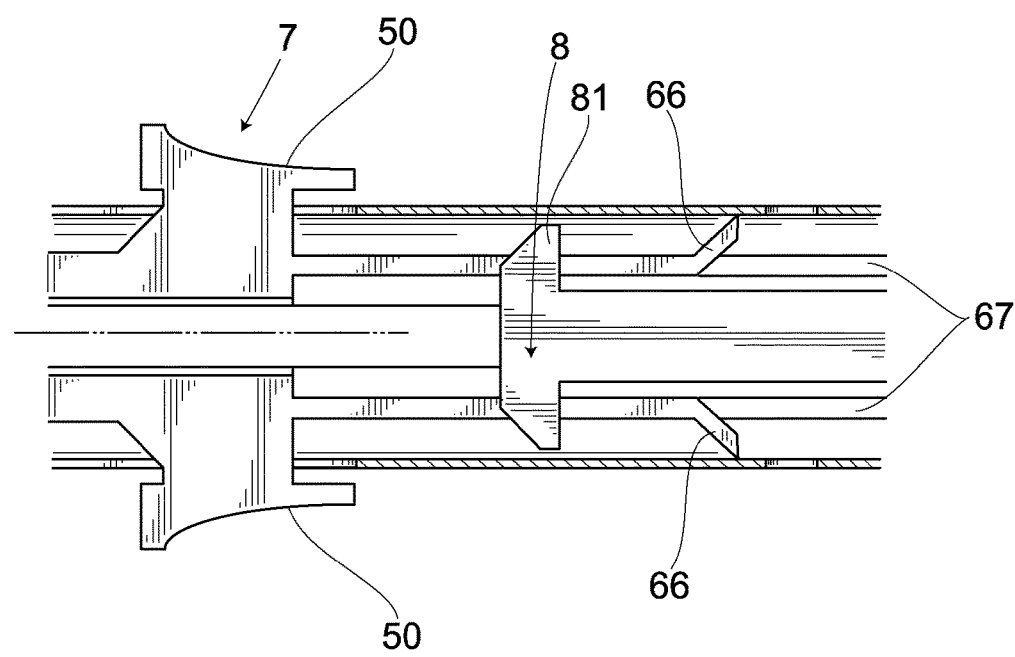
FIG. 32 is a partial cross-sectional view showing the operation.

As the slider 7 is pushed out, locking of the plunger 8 by the lock mechanism 9 is released. That is, as the slider 7 is pushed out, engagement of the latching parts 66, 66 and the second protrusion 88 provided on the circular disk part 81 of the plunger main body 72 are released. Accordingly, the locking of the plunger 8 is released, and the plunger 8 becomes movable frontward while engaging the tilting parts 65 with the release grooves 86, 86 of the circular disk part 81 (see, FIG. 32).

As explained above, because the slider 7 has the extending parts 67, 67, the position of the tilting parts 65 provided on the slider 7 is maintained so as not to be shifted with respect to the release grooves 86 of the plunger main body 72 even when the slider 7 is moved frontward. Therefore, when the slider 7 is moved frontward, the release grooves 86 and the tilting parts 65 can surely engage with one another. Accordingly, it is possible to surely fit the tilting parts 65, 65 into the respective release grooves 86, 86 after the slider 7 is moved, so that the locking of the plunger 8 is surely released, enabling the plunger 8 to be pushed out.

Figure 29D:
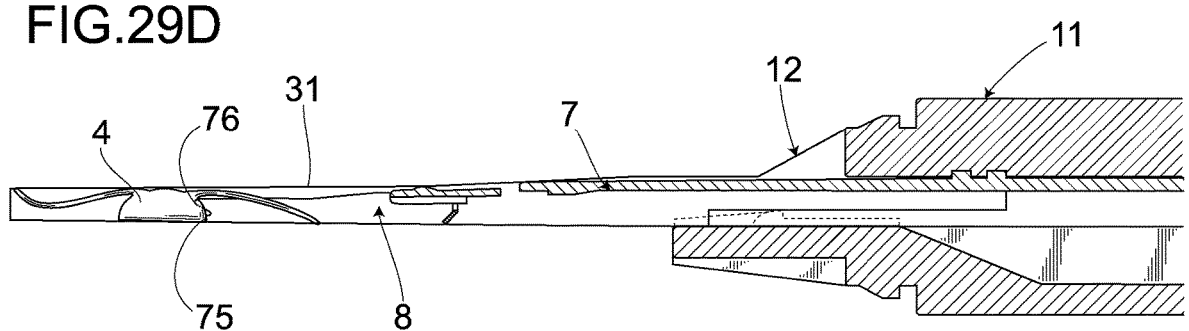

The released plunger 8 performs the second stage of movement and deformation on the intraocular lens 4 deformed in the predetermined shape by the slider 7. That is, as the plunger 8 is pushed out frontward through the guide groove 48 provided in the one side of the slider 7, the lens contact part 75 contacts the outer edge 4*c* of the intraocular lens 4 deformed in the predetermined shape by the slider 7. The grip 73 is pushed out, and the female screw 95 is threaded with the engagement protrusion 20 of the basal end member 11. As the grip 73 is rotated in this state, the plunger 8 can be moved by a predetermined amount. As the plunger 8 is moved frontward in this manner, the intraocular lens 4 is further pushed out to the transition part 31, and is folded more compactly (see, FIG. 29D and FIG. 30E). At this time, a sliding resistance applied to the leading end of the rod 71 becomes large.

Hereinafter, an explanation will be given in detail of how the lens contact part 75 provided at the leading end of the plunger 8 contacts the outer edge 4*c* of the intraocular lens 4 with reference to FIGS. 33A, 33B, 34A and 34B.

Figure 33A:
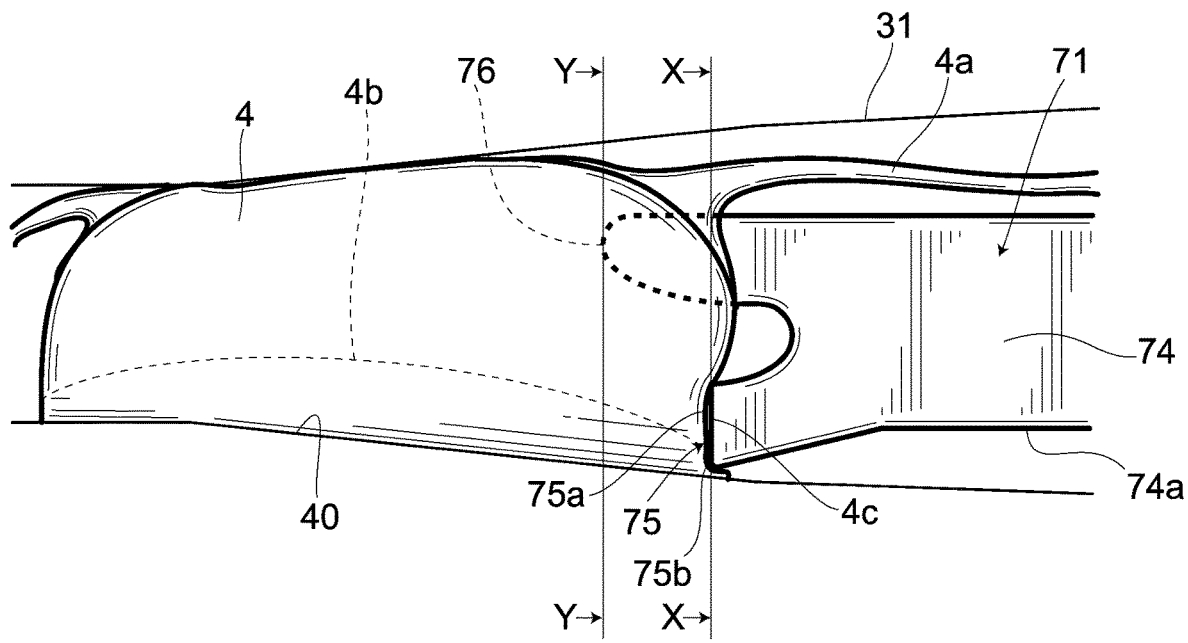
FIG. 33A is a partial enlarged side view schematically showing the operation of the device and FIG. 33B is a plan view thereof.
Figure 33B:
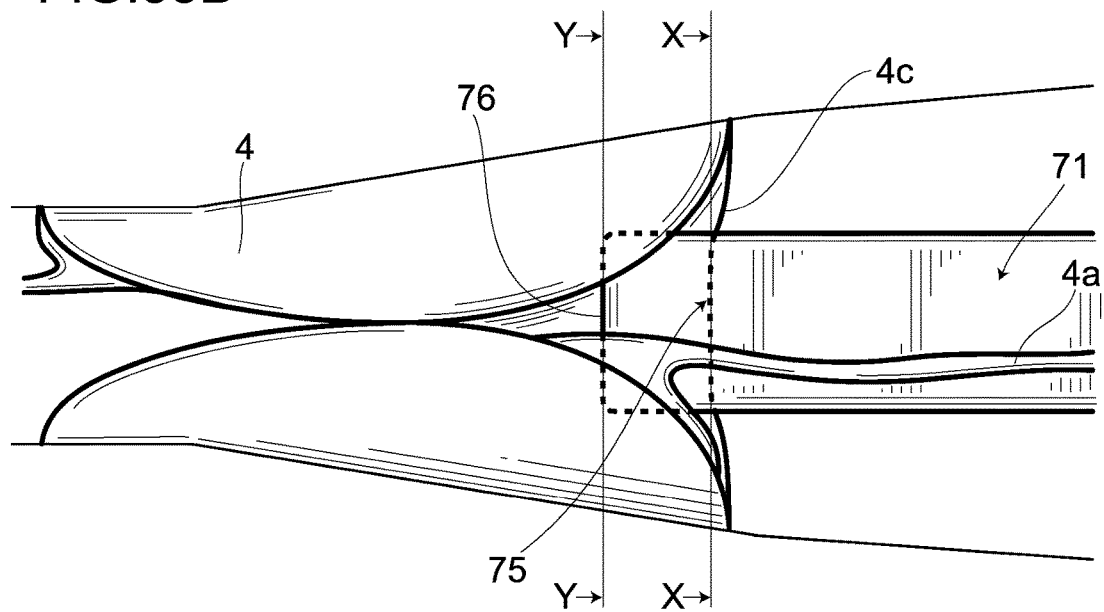
Figure 34A:
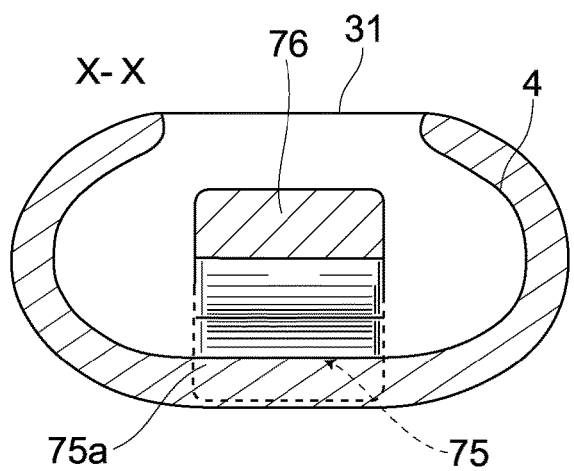
FIG. 34A is a cross-sectional view along line X-X in FIGS. 33A and 33B.
Figure 34B:
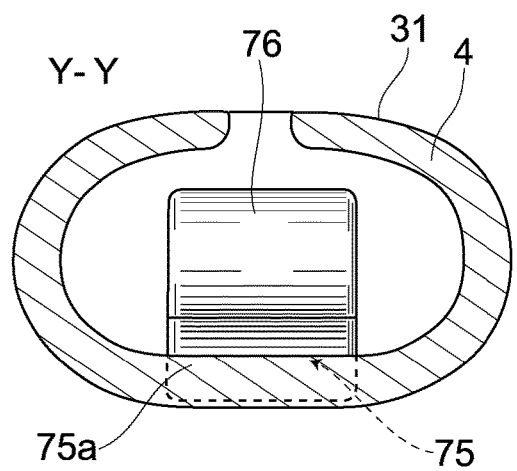
FIG. 34B is a cross-sectional view along line Y-Y in FIGS. 33A and 33B.

As shown in FIGS. 33A and 33B, the lens contact part 75 abuts the outer edge 4*c* of the intraocular lens 4 with the protrusive part 76 protruding from the outer edge 4*c* of the intraocular lens 4 toward the optical part 4*b*. As the plunger 8 is moved frontward, the lens contact part 75 bites into the outer edge 4*c* of the intraocular lens 4 and brings out an anchor effect, and moves the intraocular lens 4 to the front of the lens traveling axis A against the sliding resistance between the disposing-part bottom face 25 and the optical part 4*b* of the intraocular lens 4. Note that in the specification, the anchor effect means an effect of increasing the adhesion of the lens contact part 75 and the outer edge 4*c* of the intraocular lens 4 as the lens contact part 75 bites into the outer edge 4*c* of the intraocular lens 4.

According to a plunger 8 of the conventional technologies, when the sliding resistance caused by the intraocular lens 4 becomes large to some extent, the leading end of the plunger 8 may run on the optical part of the intraocular lens 4.

In contrast, according to the intraocular lens insertion unit 2 of the embodiment, the lens contact part 75 has the plane 75*a*, and has the one end corner 75*b* formed in a shape like a letter R having a curvature radius smaller than or equal to 70% of the thickness of the outer edge 4*c* of the intraocular lens 4. Therefore, according to the intraocular lens insertion unit 2, the lens contact part 75 contacts the outer edge 4*c* of the intraocular lens 4 with a wide area, and increases frictional force in a direction orthogonal to the lens traveling axis A. This causes frictional force in a direction orthogonal to the lens traveling axis A between the lens contact part 75 and the outer edge 4*c* of the intraocular lens 4 even if the sliding resistance caused by the intraocular lens 4 becomes large. Therefore, a better anchor effect can be achieved, thereby preventing the lens contact part 75 from moving in a direction orthogonal to the lens traveling axis A. Accordingly, the intraocular lens insertion unit 2 can prevent the leading end of the plunger 8 from running on the optical part 4*b*.

Further, the plane 75*a* of the lens contact part 75 is formed in such a way that the upper end thereof inclines backwardly with respect to the lower end, thereby facilitating the one end corner 75*b* to bite into the outer edge 4*c* of the intraocular lens 4, so that the anchor effect is easily achieved.

Figure 35A:
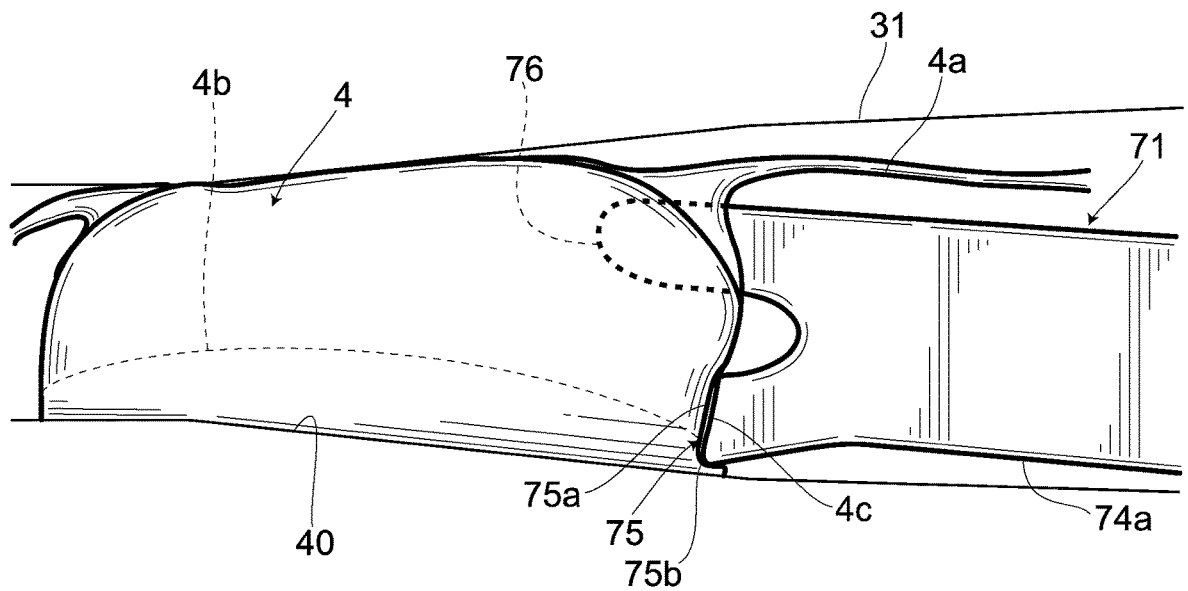
FIG. 35A is a partial enlarged side view schematically showing the operation of the device and FIG. 35B is a plan view thereof.
Figure 35B:
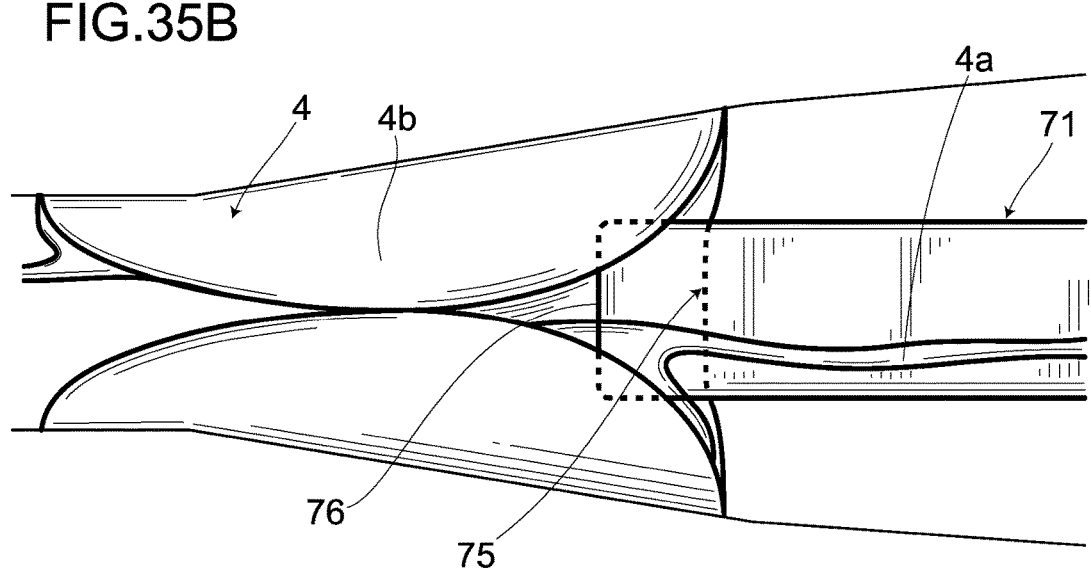
Figure 36:
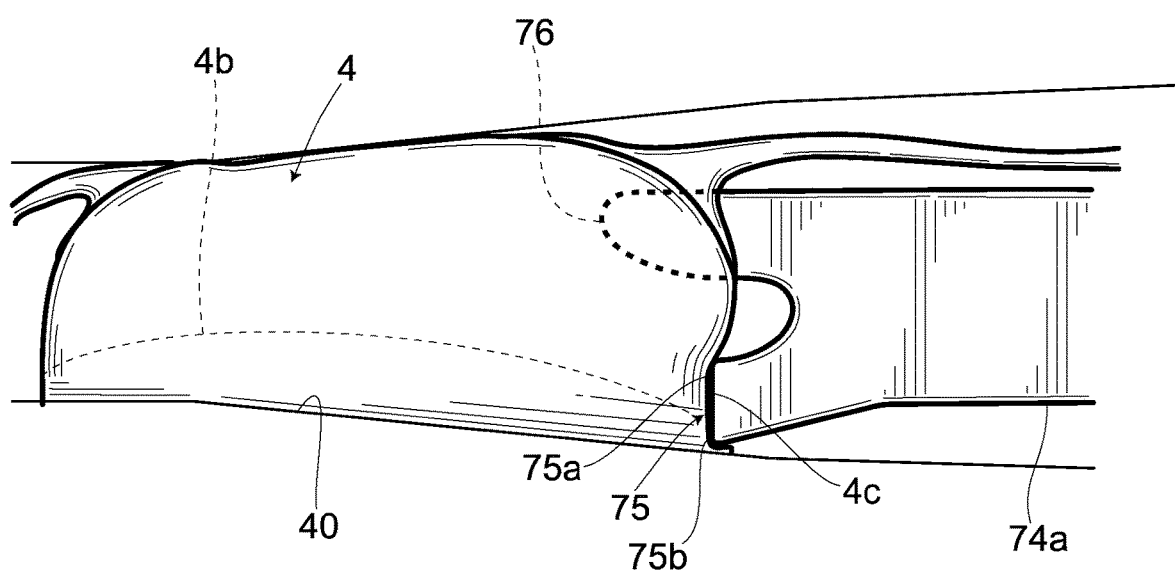
FIG. 36 is a partial enlarged side view schematically showing the operation of the device.

According to the intraocular lens insertion unit 2 (the type shown in FIG. 12B), the lens contact part 75 protrudes downwardly from the axial part 74. Therefore, even if the plunger 8 bends downwardly with respect to the lens traveling axis A in a protruding manner (see, FIGS. 35A and 35B), the plane 75*a* of the lens contact part 75 inclines upwardly, and the lens contact part 75 can be positioned below the axial part 74. This enables the one end corner 75*b* of the lens contact part 75 to bite into the outer edge 4*c* of the intraocular lens 4 in comparison with a case where the plunger 8 does not bend (see, FIG. 36) even if the plunger 8 bends downwardly with respect to the lens traveling axis A in a protruding manner and the one end corner 75*b* is apart from the lower part of the lumen 40, according to the intraocular lens insertion unit 2 of this type.

According to the plunger 8 of the embodiment, at the leading end side of the rod 71, the lower outer wall 74*a* of the axial part 74 gradually inclines toward the leading end, and the lens contact part 75 is provided at the leading end thereof in a protruding manner, and the one end corner 75*b* of the lens contact part 75 is formed in a shape like a letter R having a curvature radius smaller than or equal to the thickness of the outer edge 4*c* of the intraocular lens 4. Therefore, even if the plunger 8 bends downwardly with respect to the lens traveling axis A in a protruding manner and the one end corner 75*b* is lifted up to a certain extent from the bottom part of the lumen 40, the one end corner 75*b* can be caused to easy bite into the outer edge 4*c* of the intraocular lens 4, thereby achieving the anchor effect. Therefore, the intraocular lens insertion unit 2 can prevent the leading end of the plunger 9 from running on the optical part 4*b*.

In a case where the plunger 8 bends concavely toward the disposing-part bottom face 25 with respect to the lens traveling axis A, the lens contact part 75 located at the leading end of the plunger 8 is pressed against the bottom part of the lumen 40, thereby further surely preventing the leading end of the plunger 8 from running on the optical part 4*b*.

According to the intraocular lens insertion unit 2, the plunger 8 is formed of a synthetic resin, the plunger 8 does not apply an overload to the intraocular lens 4, thereby suppressing a damaging to the intraocular lens 4.

Further, the intraocular lens insertion unit 2 is of a preset type that is to undergone a shipment with the intraocular lens 4 being disposed on the lens disposing part 15 beforehand, so that the lens disposing part 75 can be designed and selected in accordance with the thickness of the outer edge 4*c* of the intraocular lens 4, resulting in a further ensured prevention of the leading end of the plunger 8 from running on the optical part 4*b*.

According to the intraocular lens insertion unit 2, the rod 71 has the protrusive part 76 formed at the leading end thereof. The protrusive part 76 slides into the overlapped portion of the outer edge 4*c* of the intraocular lens 4 folded as it travels in the transition part 31. Accordingly, the protrusive part 76 is relatively urged by what corresponds to the thickness of the overlapped portion of the intraocular lens 4. Namely, the protrusive part 76 receives force in a direction orthogonal to the lens traveling axis A from the intraocular lens 4 pushed and deformed by the plunger 8, and the force is applied to the lens contact part 75. The lens contact part 75 is pressed downward the optical part 4b of the intraocular lens 4 by this force. Therefore, even if the sliding resistance becomes large as the intraocular lens 4 is folded compactly, the lens contact part 75 is urged downward the optical part 4b of the intraocular lens 4, so that a lifting up of the lens contact part 75 is prevented, thereby surely preventing the plunger 8 from running on the optical part 4b.

As explained above, according to the intraocular lens insertion unit 2, the lens contact part 75 has the plane 75a, and has the one end corner 75b formed in a shape like a letter R having a curvature radius smaller than or equal to 70% of the thickness of the outer edge 4c of the intraocular lens 4, the rod 71 has the protrusive part 76 formed on the leading end thereof, and the lens contact part 75 protrudes downward the axial part 74, thereby surely preventing the plunger 8 from running on the optical part 4b even though the plunger 8 is formed of a synthetic resin and thus having a weak strength.

Further, according to the intraocular lens insertion unit 2, the upper face of the protrusive part 76 is formed in a smooth curved shape. Therefore, it is possible to prevent the optical part 4b of the intraocular lens 4 from being damaged due to the upper face of the protrusive part 76. Accordingly, the intraocular lens insertion unit 2 can cause the ejected intraocular lens 4 to achieve a desired characteristic.

Still further, according to the intraocular lens insertion unit 2, the lens contact part 75 is formed by a plane. Accordingly, it is possible to easily position the intraocular lens 4 and the leading end of the plunger 8. Therefore, the intraocular lens insertion unit 2 can surely fold the intraocular lens 4 compactly to eject it.

As explained above, the effectiveness that a running of the plunger 8 on the optical part 4b of the intraocular lens 4 is surely prevented because the plunger 8 has the protrusive part 76 provided at the leading end thereof can also be brought out by an intraocular lens insertion device which does not have the foregoing plunger 8. Namely, intraocular lens insertion devices which deform an intraocular lens while moving the intraocular lens by pushing out the intraocular lens disposed at a lens disposing part in a transition part by a plunger may employ a structure of deforming portions of an outer edge 4c of the intraocular lens across a lens traveling axis in a direction orthogonal to the lens traveling axis.

Intraocular lens insertion devices may be structured in such a way that a lens disposing part has a function of the first stage of deformation as long as the apparatuses have a function of moving an intraocular lens, or an intraocular lens deformed to some extent beforehand may be disposed on a lens disposing part.

Accordingly, a protrusive part slides into an overlapped portion of the outer edge 4c of the intraocular lens folded as it travels in a transition part 31. Thus, because the protrusive part is relatively urged by what corresponds to the thickness of the overlapped portion of the outer edge 4c of the intraocular lens in this manner, it is possible to prevent a plunger from running on the optical part of the intraocular lens.

The intraocular lens 4 is pushed out by the slider 7 and the plunger 8 in this manner from a state where the intraocular lens 4 is disposed on the lens disposing part 15, and is ejected from the nozzle 32 in a state where the intraocular lens 4 is folded compactly.

4. Modified Embodiments

The present invention is not limited to the foregoing embodiment, and can be changed and modified in various forms without departing from the scope of the invention. For example, the explanation has been given of the case where the lens holder of the slider pushes the optical part of the intraocular lens downwardly and the leading end rail lifts up the peripheral end of the intraocular lens parallel to the lens traveling direction upwardly. The invention is, however, not limited to this case, and the lens holder of the slider may push one face of the optical part of the intraocular lens upwardly, while the leading end rail may deform the peripheral end of the intraocular lens parallel to the lens traveling direction downwardly, which is a direction opposite to the foregoing one direction.

In the foregoing embodiment, the explanation has been given of the case where the intraocular lens insertion device 1 is mainly formed of a synthetic resin overall. The invention, however, is not limited to this case, and the intraocular lens insertion device 1 may be formed of a metal, such as stainless steel, or titanium.

Figure 37A:
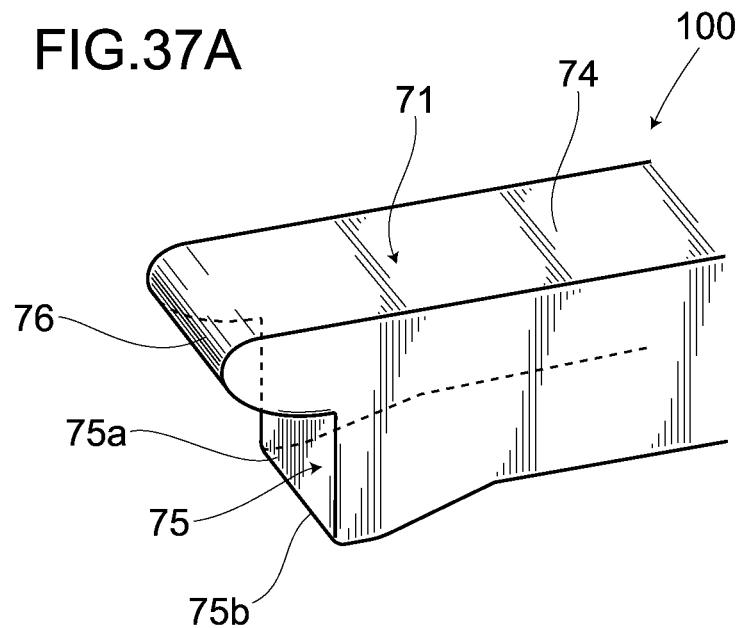
FIG. 37A is an upper perspective view showing a leading end of a rod according to a first modified embodiment and FIG. 37B is a lower perspective view thereof.
Figure 37B:
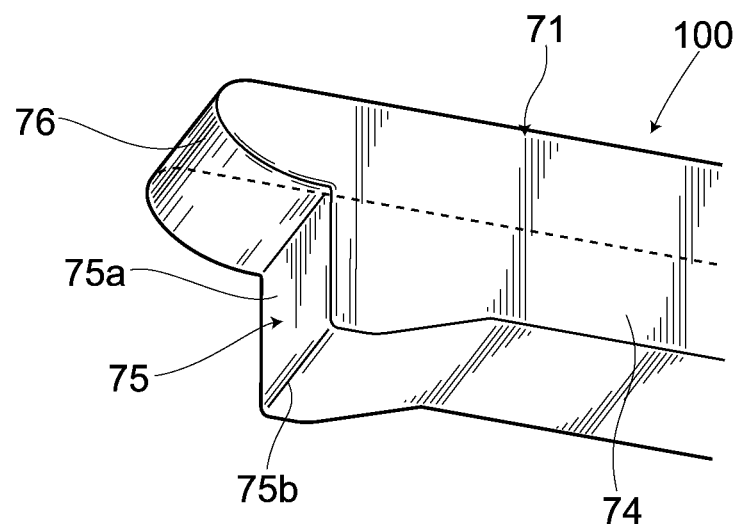

In the foregoing embodiment, the explanation has been given of the case where the recess, concaved rearwardly, is formed between the lens contact part 75 and the protrusive part 76 at the front end of the rod 71. The invention, however, is not limited to this case. Namely, as shown in FIGS. 37A and 37B, a rod 100 of a first modified embodiment has a leading end constituted by a lens contact part 75 formed substantially vertical, and a protrusive part 76.

Figure 38A:
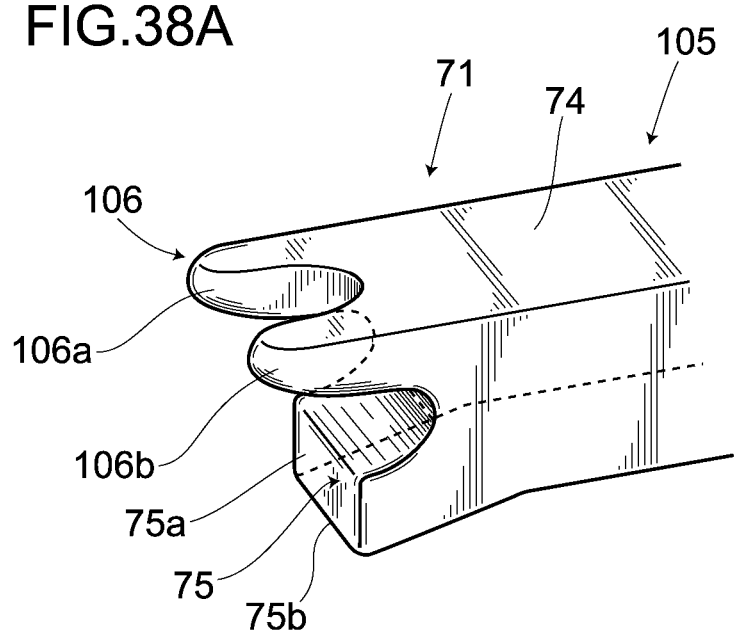
FIG. 38A is an upper perspective view showing a leading end of a rod according to a second modified embodiment and FIG. 38B is a lower perspective view thereof.
Figure 38B:
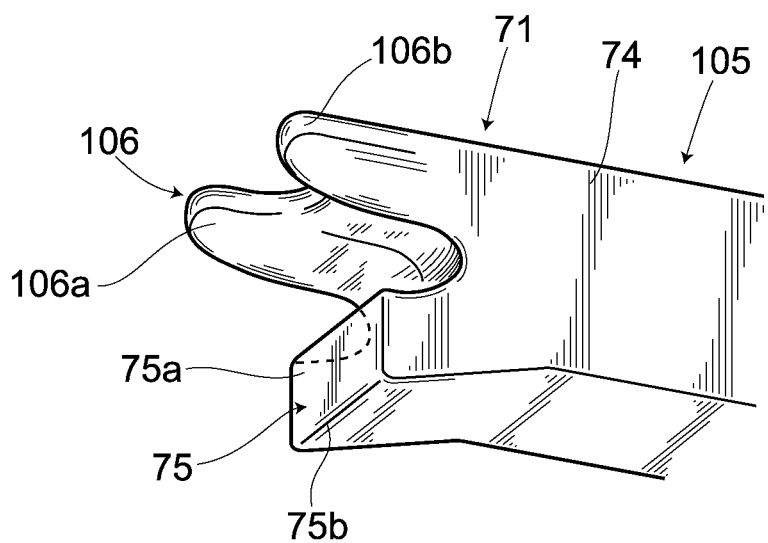

A rod 105 shown in FIGS. 38A and 38B according to a second modified embodiment has a two-forked protrusive part 106 (106a, 106b) formed at the leading end. Accordingly, when the intraocular lens 4 pushed out by the plunger 8 deforms, the protrusive part 106 can deform in a direction in which the divided leading ends become narrow by external force. This enables the narrowed leading ends of the two-forked protrusive parts 106a, 106b to absorb a load applied to the basal portion of the support part 4a of the intraocular lens 4. Therefore, the rod 105 of the second embodiment can reduce a load applied to the basal portion of the support part 4a of the intraocular lens 4, thereby preventing the basal portion of the support part 4a from being damaged. Further, the rod 105 of the second embodiment can sandwich the optical part 4b or the support part 4a of the intraocular lens 4 through the leading ends of the tow-forked protrusive parts 106a, 106b, and adjust the position of the intraocular lens 4 in an eye.

Figure 39A:
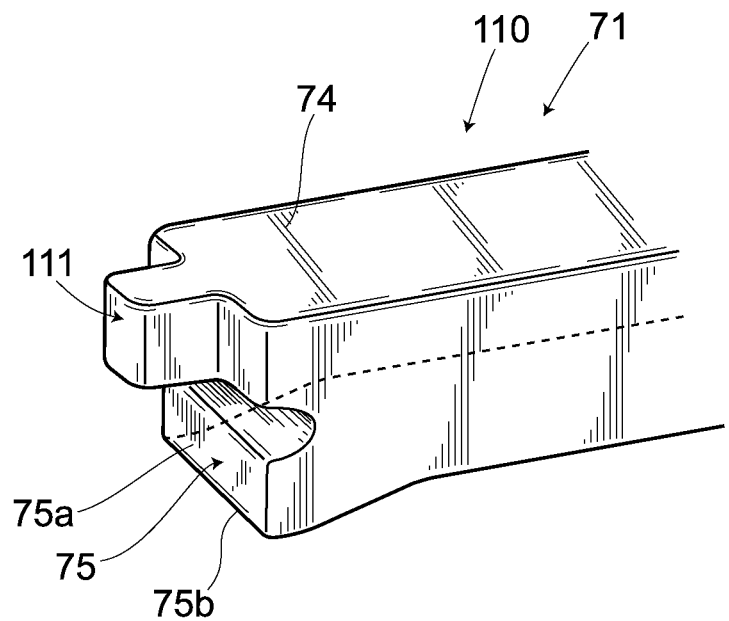
FIG. 39A is an upper perspective view showing a leading end of a rod according to a third modified embodiment and FIG. 39B is a lower perspective view thereof.
Figure 39B:
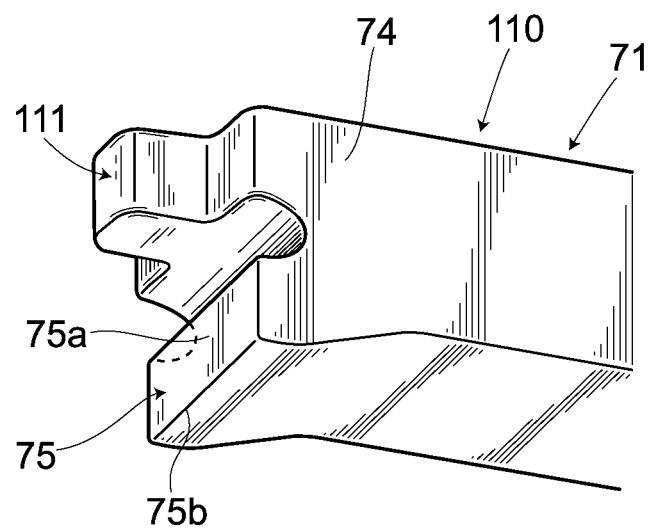

A rod 110 of a third modified embodiment shown in FIGS. 39A and 39B has a protrusive part 111 having a width which is about ⅓ of the axial part 74, and provided at the center of the leading end of the rod 71. The protrusive part 111 can easily deform with force in a direction orthogonal to the lens traveling axis A in comparison with the foregoing embodiment, and can reduce a load applied to the basal portion of the support part 4a of the intraocular lens 4 likewise the second modified embodiment, thereby preventing the basal portion of the support part 4a from being damaged.

Figure 40A:
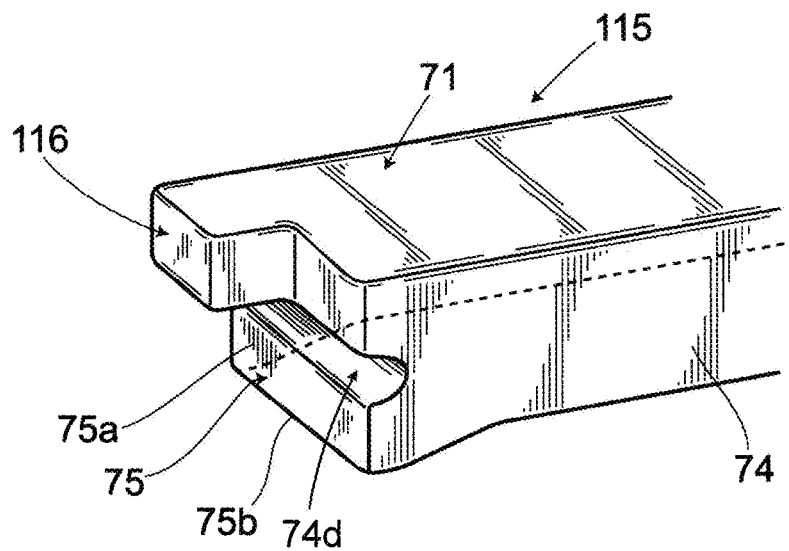
FIG. 40A is an upper perspective view showing a leading end of a rod according to a fourth modified embodiment and FIG. 40B is a lower perspective view thereof.
Figure 40B:
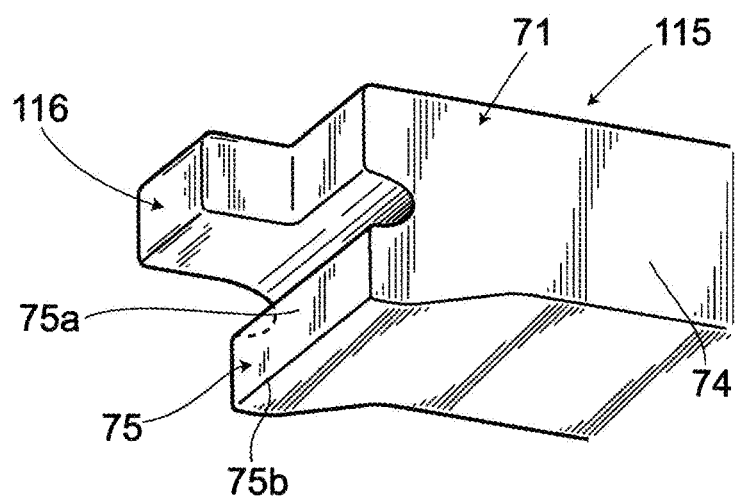

Further, a rod 115 of a fourth modified embodiment shown in FIGS. 40A and 40B has a protrusive part (or "upper protrusion") 116 having a width which is about ½ of the axial part 74, and provided at one corner of the leading end of the rod 71. A proximally extending indentation defines a slot 74*d* that is located between the protrusive part 116 and the lens contact part (or "lower protrusion") 75. The protrusive part 115 can easily deform with force in a direction orthogonal to the lens traveling axis A in comparison with the foregoing embodiment, and can reduce a load applied to the basal portion of the support part 4*a* of the intraocular lens 4 like in the second modified embodiment, thereby preventing the basal portion of the support part 4*a* from being damaged.

Figure 41A:
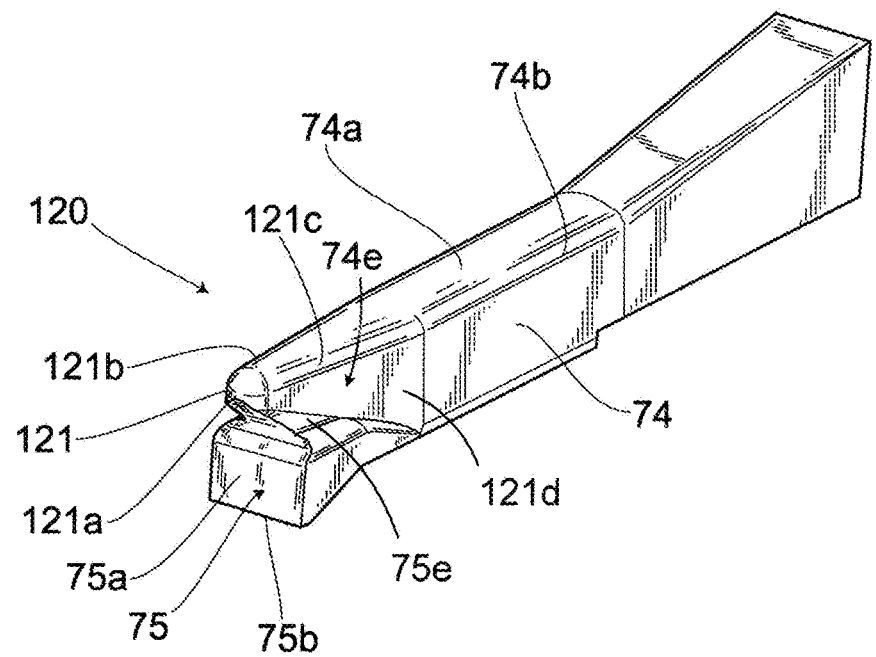
FIG. 41A is an upper perspective view showing a leading end of a rod according to a fifth modified embodiment and FIG. 41B is a lower perspective view thereof.
Figure 41B:
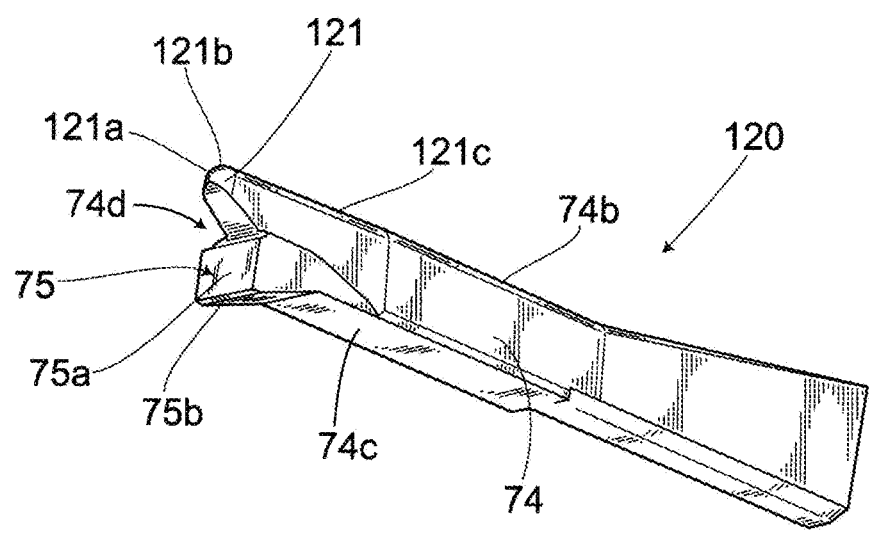

A rod 120 of a fifth modified embodiment shown in FIGS. 41A and 41B has a protrusive part 121 tapered toward a leading end of the rod 120. Further, the leading end 121*a*, an upper end 121*b*, and an upper corner 121*c* of the protrusive part 121 are each formed in a smoothly curving manner. The upper surface 74*a* and corner 74*b* of the axial part 74 are also formed in a smoothly curving manner, specifically in a portion where the axial part 74 and the support part 4*a* of the intraocular lens 4 are overlapped with each other. Thus, when the intraocular lens 4 is ejected out, a rear support part 4*a* staying between the axial part 74 and the nozzle 32 can be smoothly pushed out into an eye as the shape of the optical part 4*b* is gradually restored. The axial part 74 also includes a lower surface 74*c*. The lens contact part 75 and the protrusive part 121 together define a slot 74*d* therebetween. The taper of the protrusive part 121 also results in indentations 74*e* that are defined by the contact part top wall 75*e* and the protrusive part side walls 121*d*.

Although the explanation has been given of the case where the lens contact part 75 is a plane in the foregoing embodiment, the invention is not limited to this case, and the lens contact part 75 can be structured in such a manner as to increase frictional force with the outer edge of the intraocular lens. For example, the lens contact part 75 may have a rough face, or a groove running in the vertical direction and the horizontal direction, or may have a protrusion which bites into the outer edge of the intraocular lens.

The invention claimed is:

1. A method, comprising the steps of:
    pushing an intraocular lens with a plunger along a lens travelling axis within an intraocular lens insertion apparatus, the plunger including a rod having a proximal portion and a distal axial portion with an upper protrusion defining a distal end, first and second lateral surfaces on opposite sides of the lens travelling axis, and an uppermost surface that extends from the from the first lateral surface to the second lateral surface, a lower protrusion defining a distal end that is offset from the distal end of the upper protrusion in a direction defined by the lens travelling axis, a slot between the upper and lower protrusions, and an indentation, formed by non-parallel walls which intersect with one another at an intersection, that extends proximally from the upper protrusion; and
    applying a force to the upper protrusion in a direction orthogonal to the lens travelling axis.

2. A method as claimed in claim 1, wherein
    the force is applied to the upper protrusion by a folded portion of the intraocular lens.

3. A method as claimed in claim 1, wherein
    the indentation defines a first indentation; and
    the plunger further includes a second indentation that extends proximally from the upper protrusion.

4. A method as claimed in claim 1, wherein
    the intraocular lens insertion apparatus includes a main body including an intraocular lens storage region, a tapered transition part and a nozzle; and
    the force is applied as the upper protrusion moves through the tapered transition portion.

5. A method as claimed in claim 1, wherein
    the upper protrusion includes a rounded end.

6. A method as claimed in claim 1, wherein
    the intraocular lens includes an optical part and support parts;
    the plunger includes a lens contact surface; and
    pushing the intraocular lens comprises pushing intraocular lens optical part with the lens contact surface.

7. A method as claimed in claim 1, further comprising the step of:
    storing the intraocular lens in the intraocular lens insertion apparatus.

8. A method as claimed in claim 1, further comprising the step of:
    pushing the intraocular lens with a slider prior to pushing the intraocular lens with the plunger.

9. A method as claimed in claim 1, wherein
    the uppermost surface comprises a convex curved uppermost surface.

10. A method, comprising the step of:
    pushing an intraocular lens with a plunger along a lens travelling axis within an intraocular lens insertion apparatus, the plunger including a rod having a proximal portion and a distal axial portion with an upper protrusion defining a distal end, a proximal end, and a width perpendicular to the lens travelling axis that increases from the distal end, a lower protrusion defining a distal end that is offset from the distal end of the upper protrusion in a direction defined by the lens travelling axis, a slot between the upper and lower protrusions, and an indentation, formed by non-parallel walls which intersect with one another, that extends proximally from the upper protrusion and that has a proximal end at the proximal end of the upper protrusion.

11. A method as claimed in claim 10, wherein
    the indentation defines a first indentation; and
    the plunger further includes a second indentation that extends proximally from the distal end of the upper protrusion.

12. A method as claimed in claim 10, wherein
    the intraocular lens includes an optical part and support parts;
    the plunger includes a lens contact surface; and
    pushing the intraocular lens comprises pushing intraocular lens optical part with the lens contact surface.

13. A method as claimed in claim 10, further comprising the step of:
    storing the intraocular lens in the intraocular lens insertion apparatus.

14. A method as claimed in claim 10, further comprising the step of:
    pushing the intraocular lens with a slider prior to pushing the intraocular lens with the plunger.

15. A method as claimed in claim 10, further comprising the step of:
    applying a force to the upper protrusion in a direction orthogonal to the lens travelling axis.

16. A method as claimed in claim 15, wherein
    the force is applied to the upper protrusion by a folded portion of the intraocular lens.

17. A method as claimed in claim 15, wherein
    the intraocular lens insertion apparatus includes a main body including an intraocular lens storage region, a tapered transition part and a nozzle; and the force is applied as the upper protrusion moves through the tapered transition portion.

\* \* \* \* \*